(12) United States Patent
Hewson et al.

(10) Patent No.: US 11,458,255 B2
(45) Date of Patent: Oct. 4, 2022

(54) DOSE SETTING AND INDICATOR MECHANISM

(71) Applicant: NORTON HEALTHCARE LIMITED, West Yorkshire (GB)

(72) Inventors: Karl James Hewson, Cambridgeshire (GB); George Bostock, Cambridgeshire (GB); George Robert Michael Savell, Cambridgeshire (GB); James Alexander Davies, Cambridgeshire (GB); Oliver Hart, Cambridgeshire (GB); Joshua Arieh Shenker, Cambridgeshire (GB)

(73) Assignee: Norton Healthcare Limited, Castleford (GB)

( * ) Notice: Subject to any disclaimer, the term of this patent is extended or adjusted under 35 U.S.C. 154(b) by 57 days.

(21) Appl. No.: 16/332,025

(22) PCT Filed: Sep. 11, 2017

(86) PCT No.: PCT/EP2017/072777
§ 371 (c)(1),
(2) Date: Mar. 11, 2019

(87) PCT Pub. No.: WO2018/046735
PCT Pub. Date: Mar. 15, 2018

(65) Prior Publication Data
US 2019/0358408 A1 Nov. 28, 2019

(30) Foreign Application Priority Data
Sep. 12, 2016 (GB) ...................................... 1615433

(51) Int. Cl.
*A61M 5/315* (2006.01)
*A61M 5/20* (2006.01)
(Continued)

(52) U.S. Cl.
CPC ...... *A61M 5/31553* (2013.01); *A61M 5/2033* (2013.01); *A61M 5/24* (2013.01);
(Continued)

(58) Field of Classification Search
CPC .......... A61M 5/31553; A61M 5/31585; A61M 2005/3126; A61M 5/31583;
(Continued)

(56) References Cited

U.S. PATENT DOCUMENTS

| 8,672,898 B2 | 3/2014 | Enggaard |
| 2006/0153693 A1 | 7/2006 | Fiechter et al. |

(Continued)

FOREIGN PATENT DOCUMENTS

| FR | 2531879 A1 | 2/1984 |
| WO | 2006/045528 A1 | 5/2006 |

(Continued)

OTHER PUBLICATIONS

International Search Report and Written Opinion, PCT/EP2017/072777, dated Dec. 11, 2017, 18 pages.

*Primary Examiner* — Amber R Stiles
*Assistant Examiner* — Avery Smale
(74) *Attorney, Agent, or Firm* — BakerHostetler

(57) ABSTRACT

An injection device comprising a housing (112), and a dose selector (116) operatively connectable to a dose indicator positioned within the housing. The dose selector and the dose indicator (118, 119) are capable of cooperating to set a dose to be ejected from the injection device. The injection device further comprises a spring (120) capable of storing energy necessary for ejecting the dose from the injection device. The spring is locked to the dose indicator such that a charging force can be transferred from the dose selector to the spring via the dose indicator to increase the energy stored by the spring.

15 Claims, 38 Drawing Sheets

(51) Int. Cl.
*A61M 5/24* (2006.01)
*A61M 5/31* (2006.01)
(52) U.S. Cl.
CPC .... *A61M 5/31541* (2013.01); *A61M 5/31585* (2013.01); *A61M 2005/3126* (2013.01)
(58) Field of Classification Search
CPC .................. A61M 5/2033; A61M 5/24; A61M 2005/3125; A61M 5/31526; A61M 5/31525; A61M 5/31528; A61M 5/3155
See application file for complete search history.

(56) References Cited

U.S. PATENT DOCUMENTS

2015/0174335 A1* 6/2015 Roervig ............ A61M 5/31553 604/198
2016/0058952 A1* 3/2016 Higgins ............ A61M 5/31553 604/209

FOREIGN PATENT DOCUMENTS

| | | | |
|---|---|---|---|
| WO | 2007/063342 A1 | 6/2007 | |
| WO | 2013/087574 A1 | 6/2013 | |
| WO | 2013/178372 A1 | 12/2013 | |
| WO | 2014/166900 A1 | 10/2014 | |
| WO | 2014/166905 A1 | 10/2014 | |
| WO | 2014/166908 A1 | 10/2014 | |
| WO | 2014/166909 A1 | 10/2014 | |
| WO | WO-2014166909 A1 * | 10/2014 | ........ A61M 5/31551 |
| WO | 2015/007810 A1 | 1/2015 | |
| WO | 2015/007820 A1 | 1/2015 | |
| WO | WO-2015007820 A1 * | 1/2015 | ........ A61M 5/31553 |
| WO | 2015/032772 A1 | 3/2015 | |
| WO | 2016/001299 A1 | 1/2016 | |
| WO | 2016/055438 A1 | 4/2016 | |
| WO | 2016/055623 A1 | 4/2016 | |

* cited by examiner

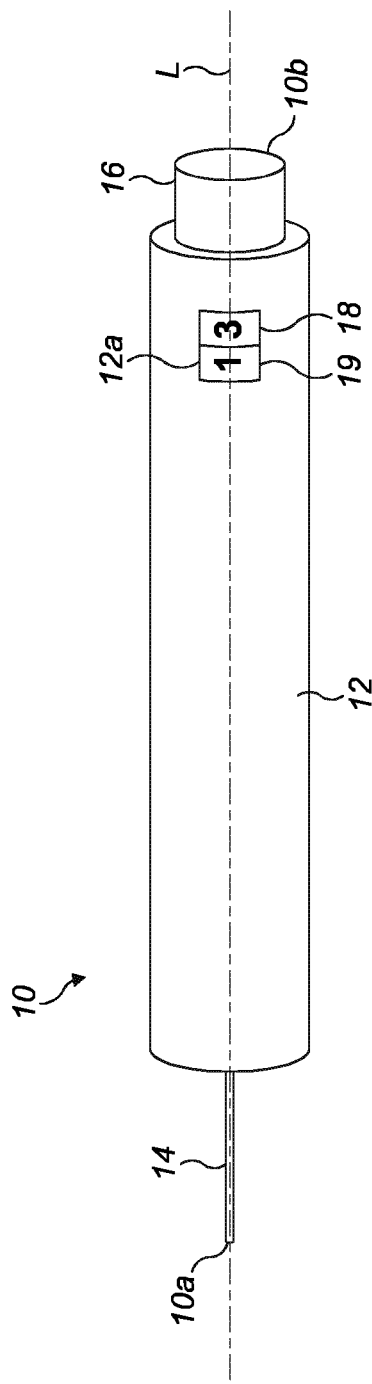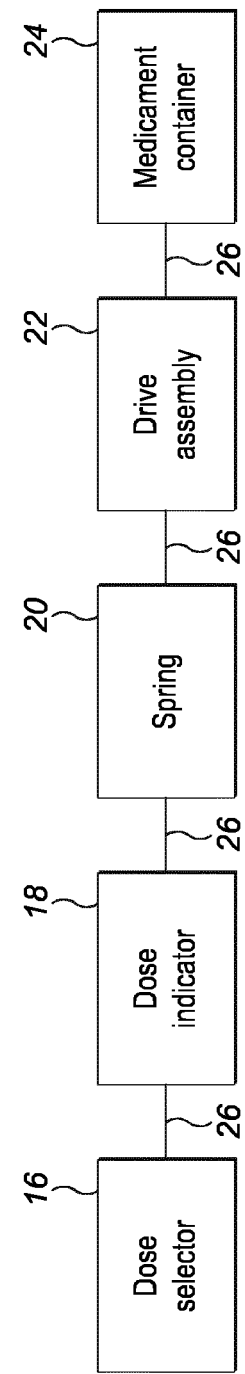

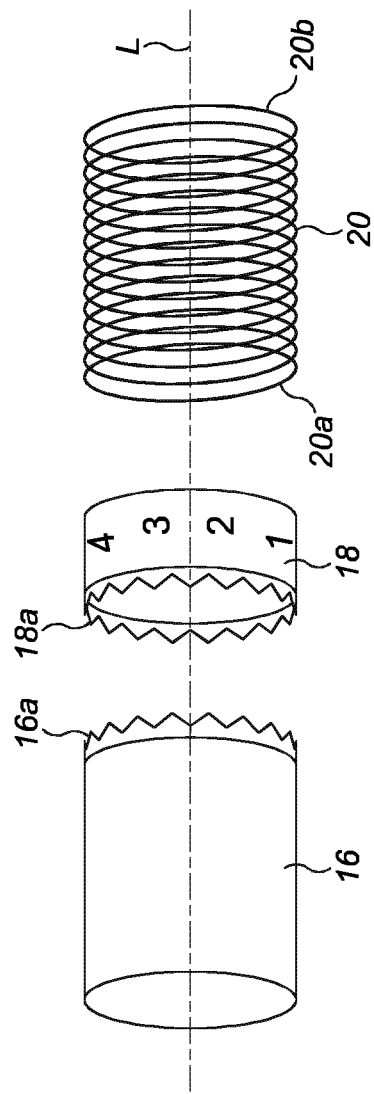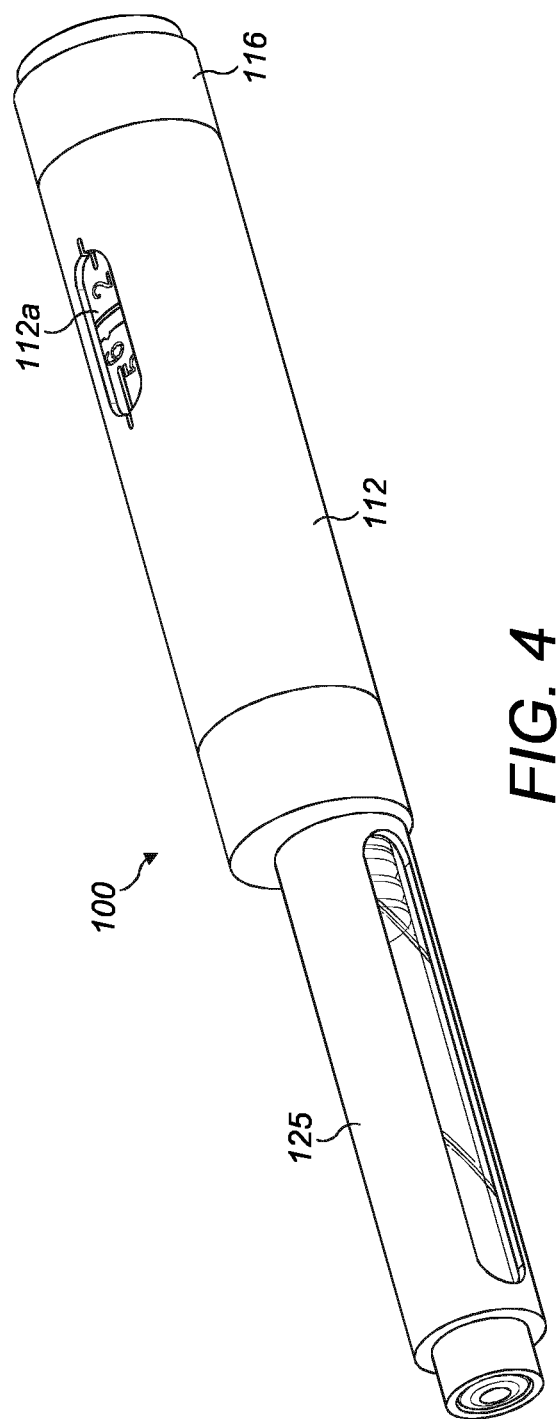

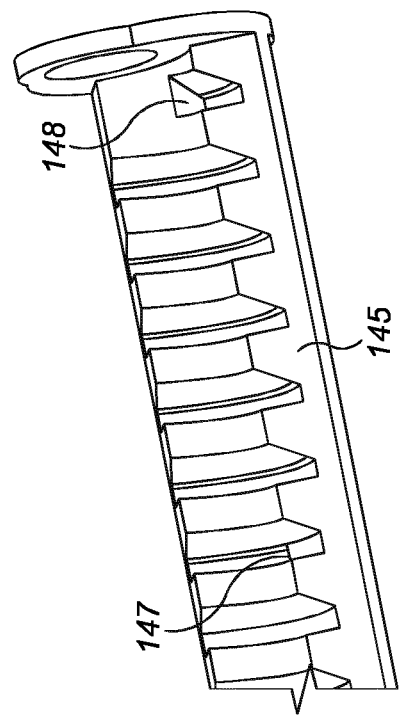
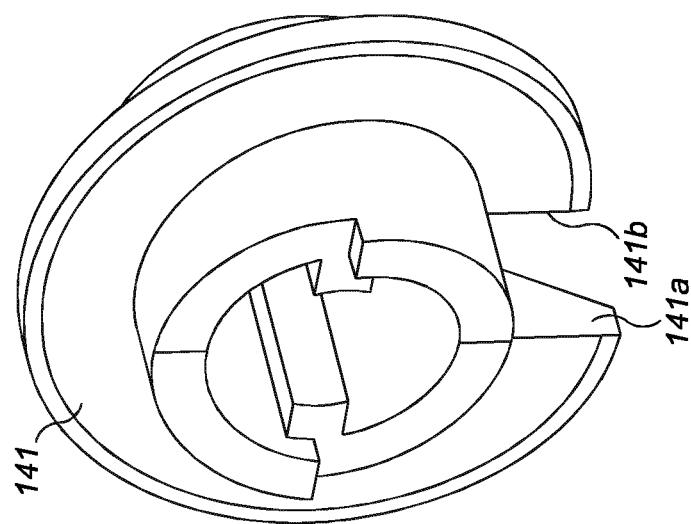

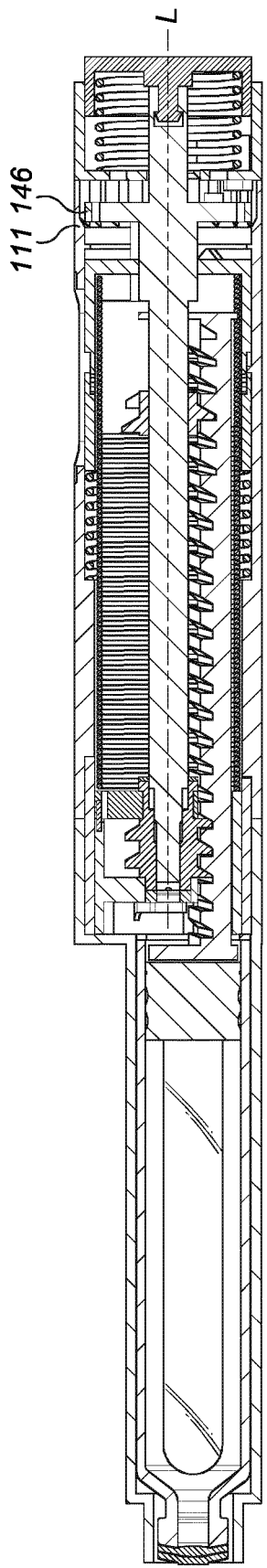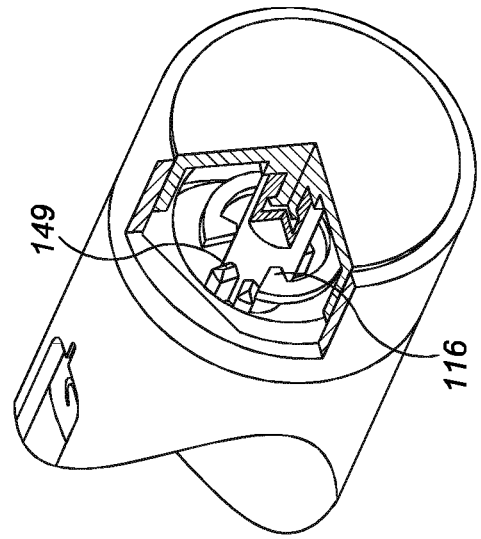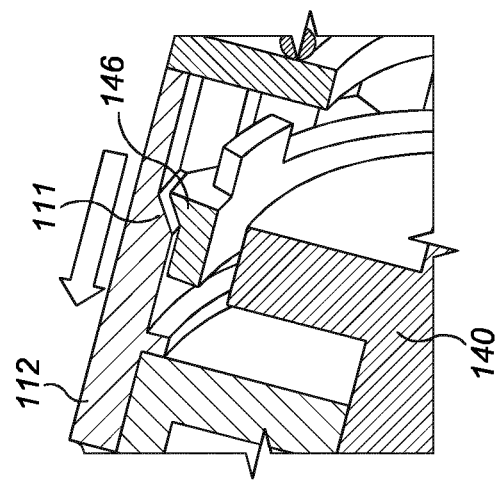
FIG. 12
FIG. 12B
FIG. 12A

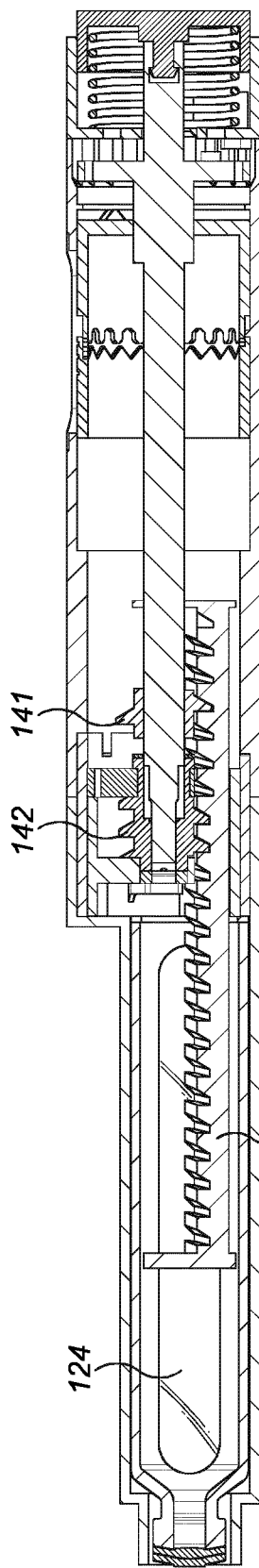
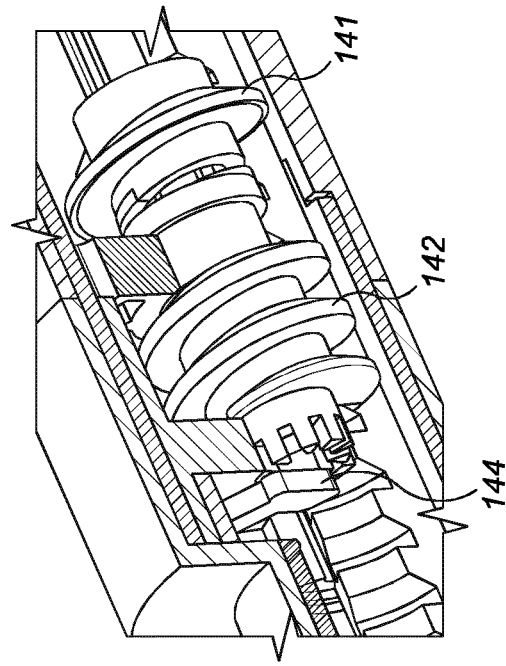
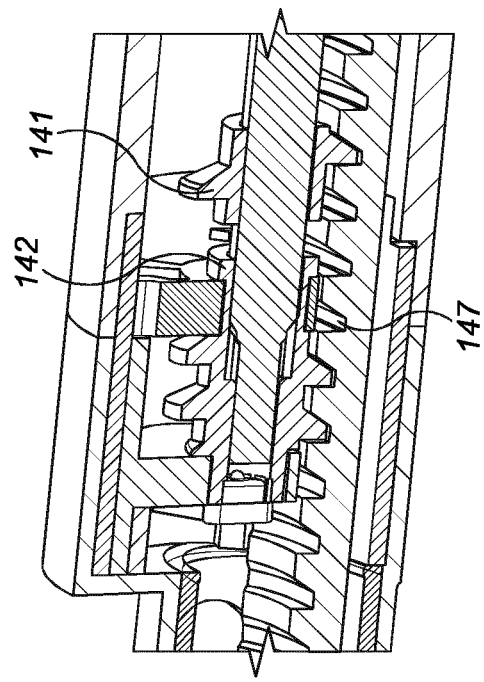
FIG. 14
FIG. 14B
FIG. 14A

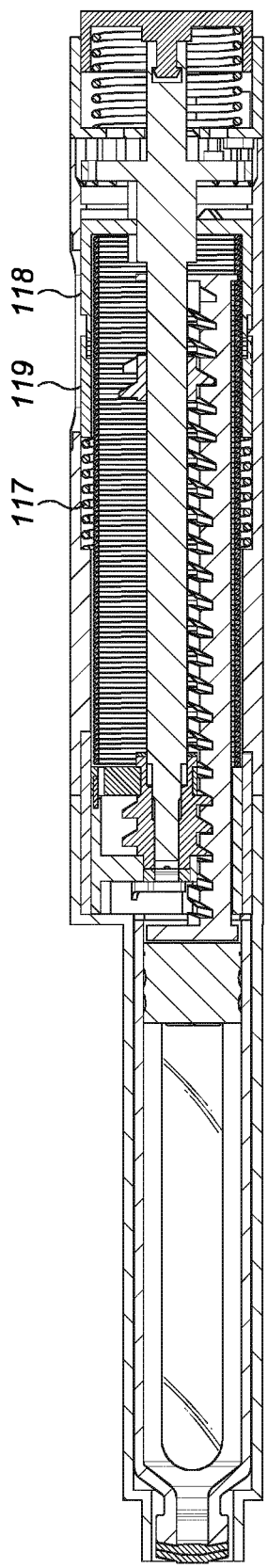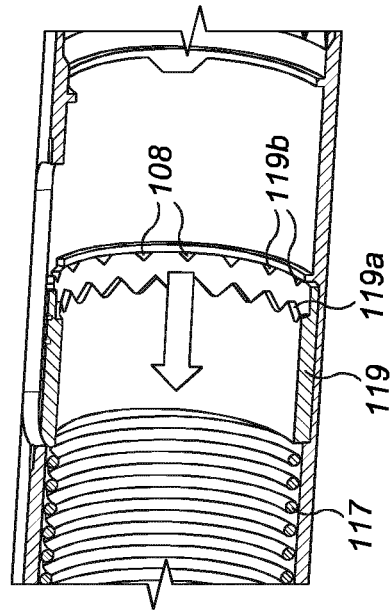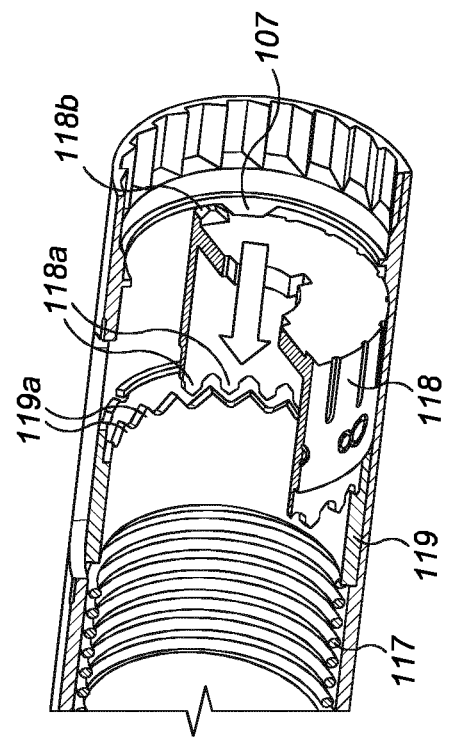
FIG. 19
FIG. 19A
FIG. 19B

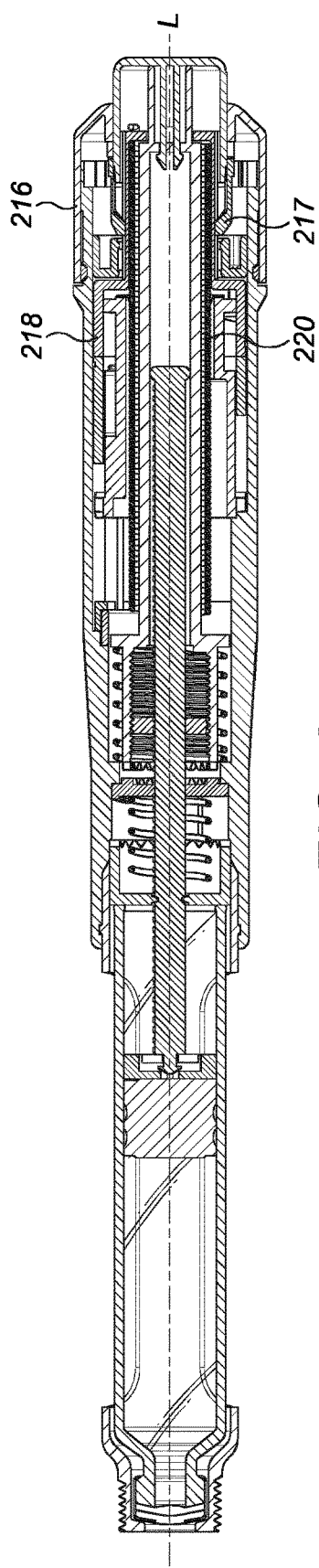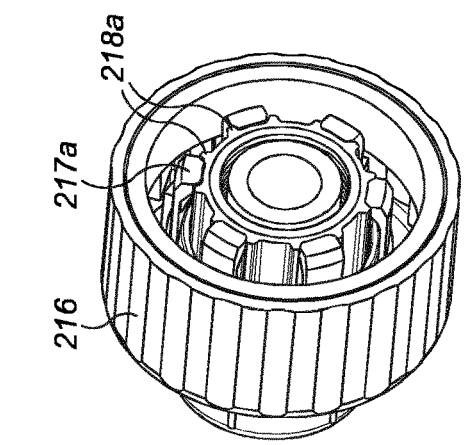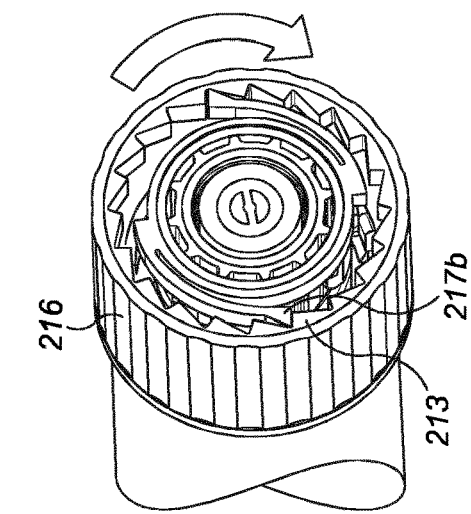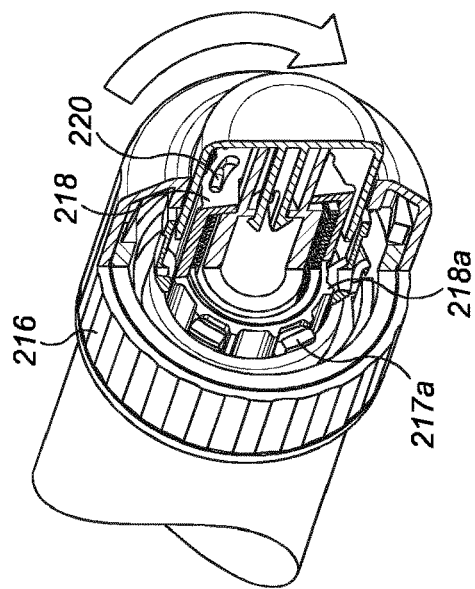
FIG. 25
FIG. 25C
FIG. 25B
FIG. 25A

DOSE SETTING AND INDICATOR MECHANISM

CROSS-REFERENCE TO RELATED APPLICATIONS

This application is the National Stage of International Patent Application No. PCT/EP2017/072777, filed Sep. 11, 2017, which claims priority from Great Britain Patent Application No. 1615433.8 filed Sep. 12, 2016, the entire contents of both of which applications are incorporated herein by reference.

This disclosure relates to the field of dose setting and dose indicator mechanisms for injection devices, preferably to dose setting and dose indicator mechanisms having a torsion spring for assisting injection of a dose of medicament from an injection device.

BACKGROUND

Certain injection devices are required to have a visual indicator for the user so that the correct dose of medicament can be set and observed. This dose indicator commonly takes the form of a number sleeve, an example of which is described in U.S. Pat. No. 8,672,898. A rotatable sleeve with numbers printed along a helical line can be inspected through a window in the housing of the device, the window showing only one of the numbers at a time which corresponds to the dose set. However, U.S. Pat. No. 8,672,898 uses a linear compression spring. An example of a number sleeve in an injection device using a torsion spring is described in WO2014/166908.

A disadvantage of using a number sleeve to indicate the dose is that the indicator area takes up a relatively large portion of the device and is generally centrally located, as illustrated in FIG. 2 of WO2014/166908. Desirably, the dose indicator needs to avoid areas of the device where the user will grip the device, so that the user's fingers do not obscure the dose indication.

An alternative type of dose indication is provided by an odometer or "units and tens" wheels or ciphers arrangement in place of a number sleeve. An example is given in WO2006/045528. Two wheels, each carrying the ten ciphers from "0" to "9" are used wherein the "tens" wheel is rotated one increment every time the "units" wheel is rotated one full revolution so that the two wheels between them can form all of the numbers from "00" to "99" in a display window. An odometer has an advantage over a number sleeve as a dose indicator in that it can be located further rearwardly towards the proximal end of the device where it is less likely to interfere with the user's finger position.

In WO2006/045528, when the dose setting member is rotated, a torsion spring is charged or strained, ready to deliver the appropriate dose. At the same time, and in parallel, the display wheels can be rotated by a planet gear 17 to display the dose which has been set.

In WO2007/063342, dose indication is provided by a number sleeve which is built in to a dose knob which charges the spring.

BRIEF SUMMARY OF THE DISCLOSURE

In accordance with an aspect of the present invention there is provided an injection device comprising:
a. a housing having a longitudinal axis;
b. an axially-depressible dose button;
c. a dose indicator comprising an odometer positioned within the housing and arranged about said longitudinal axis;
d. a dose selector operatively connectable to the dose indicator, the dose selector and the dose indicator being capable of cooperating with one another to set a dose to be ejected from the injection device; and
e. a spring capable of storing energy necessary for ejecting the dose from the injection device;
wherein the spring is locked at one end to the dose indicator such that a charging force can be transferred from the dose selector to the spring via the dose indicator, when the dose selector is operatively connected to the dose indicator, to increase the energy stored by the spring.

By coupling the spring to the dose indicator, a more accurate dose indication may be achieved. When the dose selector is rotated by a user, the dose indicator which is in series therewith serves a dual function of both displaying the currently selected dose and also transferring the charging force from the dose selector in order to charge the spring.

During delivery of a dose by the injection device, the spring releases the stored energy to deliver the dose of medicament. If the dose indicator remains coupled to the spring during delivery, the dose indicator will continue to actively reflect the current state of the spring as the spring discharges.

Embodiments of the invention are therefore advantageous over prior art arrangements in which the dose indicator is passively operated in parallel to the charging of the spring.

In certain embodiments, the dose selector is operatively connectable to the dose indicator via a ratchet pawl, the ratchet pawl releasably engaging the dose selector and preventing counter-rotation of the dose indicator during dose setting, the ratchet pawl being disengageable from the dose selector by axial depression of the dose button. In an embodiment, the charging force can be transferred from the dose selector to the spring via the engaged ratchet pawl and dose indicator.

In certain embodiments, the spring may be a torsion spring such that the charging force transferred to the spring is a charging torque. The injection device may further comprise a drive assembly having a rotational to axial coupling, where the drive assembly is rotationally drivable by the torsion spring and is arranged to provide an axial force for ejecting the dose from the injection device. The drive assembly may be rotationally drivable by the torsion spring via the dose indicator.

In certain embodiments the spring may be directly locked to the dose indicator. In alternative embodiments, the spring may be locked to the dose indicator via one or more intermediate components capable of transmitting the charging force.

Additionally or alternatively, the dose selector may be directly coupled to the dose indicator. Alternatively, the dose selector may be coupled to the dose indicator via one or more intermediate components capable of transmitting the charging force.

The dose indicator may be marked with a sequence of numbers or symbols, where at least one of the numbers or symbols may be visible through an aperture or window in the housing.

In certain embodiments, the odometer may comprise:
a units wheel operatively connected to the dose selector so that rotation of the dose selector also rotates the units wheel; and
a tens wheel selectively engageable with the units wheel so that rotation of the units wheel also rotates the tens wheel.

The injection device may further comprise a medicament container, where the medicament container may comprise a pre-filled syringe or cartridge. The injection device may further comprise a medicament contained in the medicament container. In certain embodiments, the medicament may be selected from the group comprising: antipsychotic substances including risperidone, hormones, antitoxins, substances for the control of pain, immunosuppressives, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity.

BRIEF DESCRIPTION OF THE DRAWINGS

Embodiments of the invention are further described hereinafter, by way of example only, with reference to the accompanying drawings, in which:

FIG. 1 shows an injection device in accordance with an embodiment of the present invention;

FIG. 2 is a schematic representation of a force path of an injection device according an embodiment of the present invention;

FIG. 3 is an exploded view of selected injection device components along the force path;

FIG. 4 is a perspective view of another embodiment of the injection device;

FIG. 5A is a perspective view showing further detail of the dose limit nut;

FIG. 5B is a perspective view showing further detail of part of the plunger rack;

FIGS. 11,11A-11C, 12 and 12a-12B illustrate dose delivery;

FIGS. 14 and 14A-14E illustrate last dose protection;

FIGS. 19, 19A and 19B show how the tens wheel is incremented;

FIGS. 25 and 25A-25C illustrate incrementing the dose;

DETAILED DESCRIPTION

Figure 5:
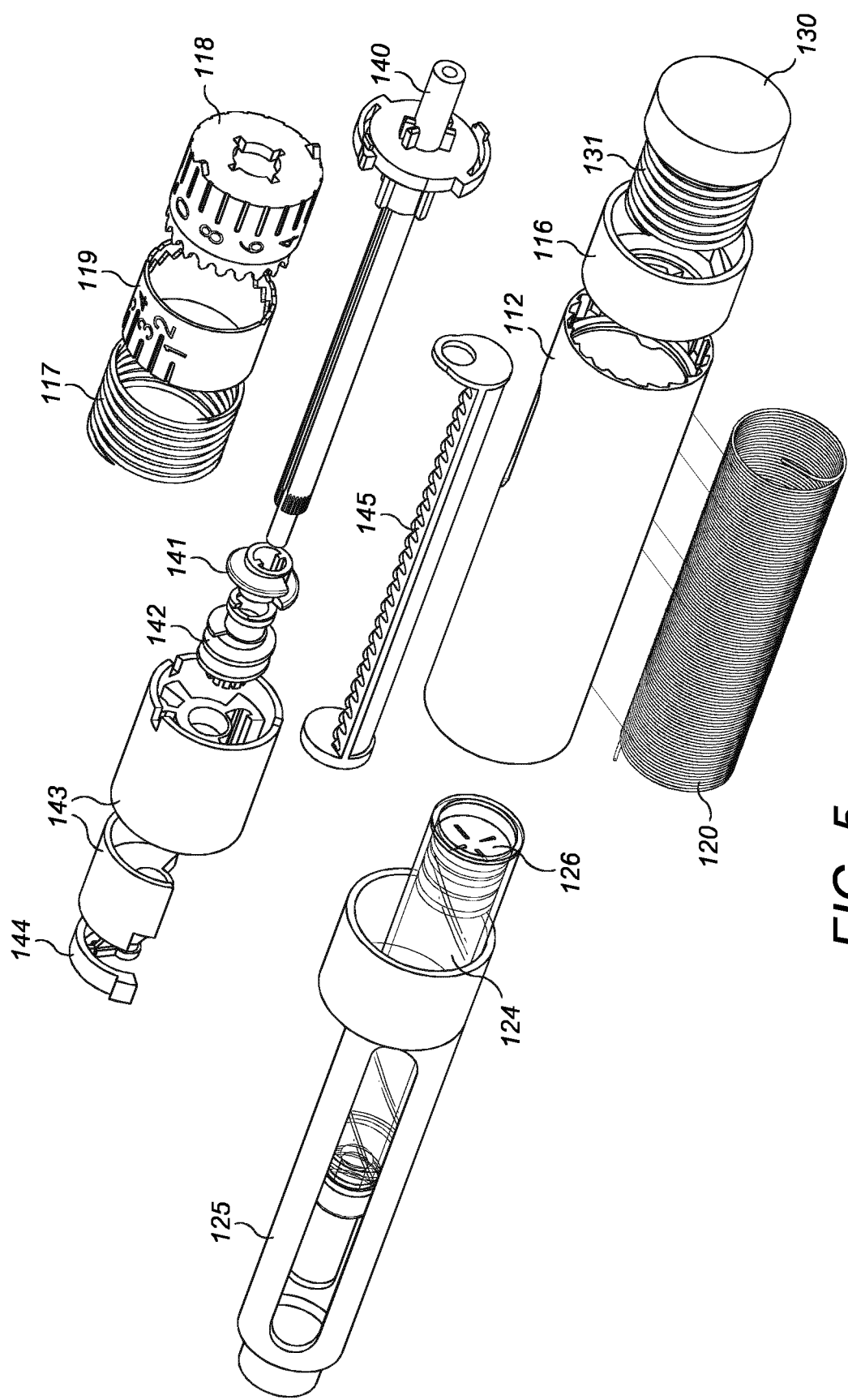
FIG. 5 is an exploded view of the injection device of FIG. 4.

In the present disclosure, the following terms may be understood in view of the below explanations:

The term "injection device" may refer to a device intended for the injection of a medicament to the body and includes devices configured for various delivery methods, such as intradermal, subcutaneous, intramuscular, intravenous, intraosseous, intraperitoneal, intrathecal, epidural, intracardiac, intraarticular, intracavernous, and intravitreal, which may include via a cannula, catheter or similar device. Injection device includes syringes of all types, devices that contain said syringes such as auto-injectors, pen-injectors, patch injectors and other similar devices.

The term "pen-injector" may include any device configured to deliver a dose of a medicament from a cartridge.

The term "user" may refer to a medical practitioner, end user or other user associated therewith.

The term "coupling" may refer to a connection between components (not necessarily a direct connection; there may be intermediate components therebetween) that enables a force to be transmitted between the components.

The term "a rotational coupling" may refer to a coupling which enables a rotational force to be transmitted between the components.

The term "operatively connectable" may refer to at least two individual components which are releasably connectable together in such a way that the individual components can work together, for example wherein rotation of one of the individual components effects rotation of all of the operatively connected components.

The term "dose selector" may refer to a component or components which, when actuated by a user, enable a dose of medicament to be selected.

The term "dose indicator" may refer to a component or components which provide a display or indication to the user of the selected dose of medicament.

The term "splines" may refer to one or more ridges, ribs or other protrusions on one component which engage in corresponding grooves or the like on a second component to connect the two components together.

The term "a splined connection" may refer to a connection effected by one or more splines.

The term "forward" or "forwards" may refer to a direction towards the end of the injection device from which medicament is expelled.

The term "backward", "backwards", "rearwards" or "rearwardly" may refer to a direction away from the end of the injection device from which medicament is expelled.

The term "drive assembly" may refer to an assembly of components capable of using a driving force from, for example, a spring, to eject medicament from an injection device.

The term "backlash" may refer to a clearance caused by a gap between mechanical components.

The term "medicament" may include a substance in liquid or gas form. The medicament may be selected from the group comprising of: antipsychotic substances including risperidone, hormones, antitoxins, substances for the control of pain, immunosuppressives, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity.

The term "containing the medicament", when referring to the injection device, may refer to the medicament being contained within a suitable medicament container, such as a pre-filled syringe or cartridge, within the injection device.

The terms "rotationally locked to" or "rotationally locked with respect to" may refer to a prevention of relative rotational movement between two rotationally locked components i.e. substantially no relative rotational movement between two rotationally locked components is possible.

The term "a force path" may refer to a path between two or more coupled components via which a force can be transmitted between the components. A force path may be "interrupted" if there is a gap between the two or more components, i.e. if they are no longer coupled. Transmission of force between coupled components may be "held back" for example by a ratchet arrangement, but in such a case the force path is not "interrupted".

The term "a clutch" may refer to a component or feature suitable for operatively connecting two component parts either by a positive fit e.g. with teeth, splines, grooves or the like suitable for engaging and disengaging each other, or by a non-positive (frictional) connection or a combination thereof. Disengaging the clutch may interrupt a force path between two or more coupled components.

Description of First Example Embodiment

An injection device 10 according to an embodiment of the present invention is shown in FIG. 1. The injection device 10 is configured to deliver a dose of medicament and extends along a longitudinal axis L between a front end 10a and a rear end 10b of the injection device 10. The injection device 10 has a housing 12 and a needle 14 projecting from the housing 12 at the front end 10a. A dose selector 16 is provided at the rear end 10b and is arranged to permit the selection of a desired dose of medicament for delivery through the needle 12 into an injection site. The housing 12 includes an aperture 12a through which a dose indicator 18 is visible.

The dose indicator 18 is disposed within the housing 12 and displays reference indicia, such as numbers or symbols, to indicate the level of dose selected by the dose selector 16. The dose indicator 18 comprises an odometer which may include a plurality of parts for indicating individual orders of magnitude of the selected dose. For example, the odometer may comprise a units wheel for displaying units and a tens wheel for displaying tens. The units wheel may be selectively engageable with the tens wheel to increment the tens wheel each time the units wheel moves through units 0 to 9.

In the preferable but non-limiting embodiment shown in FIG. 1, the aperture 12a is provided towards the rear end 10b of the injection device 10 so that the dose indicator 18 remains visible when the injection device 10 is handled by a user. The aperture 12a (and underlying dose indicator 18) may be provided elsewhere on the injection device 10 in alternative embodiments. Similarly, the dose selector 16 is shown in FIG. 1 disposed at the rear end 10b of the injection device 10 and this may be advantageous insofar as being clear of the region of the housing 12 that is likely to be gripped by a user during use of the injection device 10. In other embodiments, the dose selector 16 may be provided elsewhere.

FIG. 2 shows a schematic representation of a force path 26 within the injection device 10. In particular, the force path 26 extends between internal components of the injection device 10 that are arranged in series with one another. The internal components include the dose selector 16, the dose indicator 18, a spring 20, a drive assembly 22 and a medicament container 24. As described in further detail below, the spring 20 is configured to provide a drive force to the drive assembly 22 such that the drive assembly 22 may act to dispense medicament from the medicament container 24. A dose button (not shown), which is optionally axially-depressible, initiates dose delivery.

The dose selector 16 is coupled to the dose indicator 18 such that the indicated level of dose changes in response to manipulation of the dose selector 16. In one example, the reference indicia comprise a series of numbers and rotation of the dose selector 16 about the longitudinal axis L causes the number aligned with the aperture 12a to change according to the degree of rotation of the dose selector 16. Rotation of the dose selector 16 about the longitudinal axis L in one direction may cause the numbers to appear to increase when viewed through the aperture 12a, whereas rotation of the dose selector 16 about the longitudinal axis L in the opposite direction may cause the numbers to decrease when viewed through the aperture 12a.

The dose indicator 18 is coupled to the spring 20 such that a charging force can be transmitted from the dose selector 16 to the spring 20 via the dose indicator 18 in order to charge the spring 20. The spring 20 is charged when a force is applied to the spring 20 so as to elastically deform the spring 20, and the resulting elastic energy is stored by the spring 20 (i.e. it is prevented from elastically relaxing during a storage phase). Therefore, charging the spring 20 involves increasing the energy stored by the spring 20.

The spring 20 is coupled to the drive assembly 22 and is arranged to provide a driving force thereto when energy stored by the spring 20 is released. The drive assembly 22 acts to expel medicament from the medicament container 24. In certain embodiments, the medicament container 24 may be a syringe, vial or cartridge having a barrel and a stopper moveable in the barrel. In such embodiments, the drive assembly 22 may act to move the stopper so as to expel medicament through an opening in the barrel. In certain embodiments of the invention, the medicament cartridge may or may not be connected to a needle.

In certain embodiments, the spring 20 may be coupled to the drive assembly 22 via the dose indicator 18 and/or dose selector 16 (i.e. backwards along the force path 26 from the spring 20).

In embodiments where the spring 20 is a torsion spring, the spring 20 is charged by applying a torque to wind the spring 20 and elastic energy may be stored by the spring 20 and subsequently released as torque. In such embodiments, the force path 26 extending (at least) between the dose indicator 18 and the drive assembly 22 may be a torque path. That is, torque may be provided to the spring 20 from the dose indicator 18 and provided to the drive assembly 22 from the spring 20. In certain embodiments, the torque path extends from the dose selector 16 to the drive assembly 22 and the drive assembly 22 includes a rotational to axial coupling that is capable of then providing an axial force to a stopper in a barrel of the medicament container to expel medicament therefrom.

In embodiments where the spring 20 is a compression spring, the spring 20 may be charged by applying an axial force to compress the spring 20 and elastic energy may be stored by the spring 20 and subsequently released as an axial force.

In certain embodiments, the force path 26 may include one or more torque paths and/or one or more axial force paths, where one or more rotational to axial couplings are employed to switch between rotational and axial forces along the force path 26. Indeed, in certain embodiments, one or more intermediate components may be provided between any of the components shown in FIG. 2.

The amount of elastic energy stored by the spring 20 dictates the magnitude of the dose that is capable of being delivered. As such, the dose indicator 18 indicates the degree to which the spring 20 is charged, and thereby indicates the dose that will be delivered once the injection device 10 is actuated.

FIG. 3 shows an exploded view of the dose selector 16, the dose indicator 18 and the spring 20 arranged along the longitudinal axis L according to an embodiment of the invention. The dose selector 16 has first engaging components in the form of a first plurality of teeth 16a. The dose indicator 18 of FIG. 3 comprises an odometer that is rotatable about the longitudinal axis L and includes a series of numbers on an outer surface. The dose indicator 18 has second engaging components in the form of a second plurality of teeth 18a that are complementary to the first plurality of teeth 16a and configured to engage therewith. Engagement between the first plurality of teeth 16a and second plurality of teeth 18a forms a rotational coupling to operatively connect the dose indicator 18 to the dose selector 16 such that torque may be transferred therebetween.

In an assembled state, a first end 20a of the spring 20 is rotationally fixed to the dose indicator 18 so that the dose indicator 18 is rotationally coupled to the spring 20. For example, during assembly, the first end 20a of the spring 20 may be hooked through an aperture of the dose indicator 18, hooked to a projection of the dose indicator 18 or otherwise attached to the dose indicator 18. When the spring 20 is rotationally coupled to the dose indicator 18, torque is transferable from the dose selector 16 to the spring 20 via the dose indicator 18. A second end 20b of the spring may be attached to the drive assembly 22 (not shown in FIG. 3), and the drive assembly 22 may prevent rotation of the second end 20b of the spring 20 when the drive assembly 22 is not in an actuated state. In alternative embodiments, the second end 20b of the spring 20 may be rotationally held by a portion of the housing 12 or other component within the housing 12, and the drive assembly 22 may be coupled to the spring 20 at the first end 20a or via one or more components along the force path that extends between the dose selector 16 and the spring 20 (e.g. via the dose indicator 18 or the dose selector 16 itself).

With the second end 20b of the spring 20 rotationally held, torque transferred to the spring 20 from the dose selector 16 and dose indicator 18 will cause the spring 20 to be wound up (i.e. charged), thereby increasing the amount of elastic energy stored in the spring 20. A ratchet or other non-return mechanism may be employed to prevent the wound spring 20 from unwinding prior to use. That being said, the ratchet or other non-return mechanism may permit the deliberate incremental unwinding of the spring 20 through rotation of the dose selector 16 (i.e. when rotated in the opposite direction to the direction required to charge the spring 20). Given the rotational coupling between the dose selector 16, the dose indicator 18 and the spring 20, the ratchet or other non-return mechanism will also prevent unintended rotation of the dose selector 16 and dose indicator 18 about the longitudinal axis L due to unwinding of the spring 20.

Given that the dose indicator 18 forms an essential and integral part of the force path between the dose selector 16 and the spring 20, the dose indicator 18 actively reflects the charging state of the spring 20. Similarly, if the dose indicator 18 remains coupled to the spring 20 during discharging of the stored energy (i.e. during delivery of a dose of medicament), the dose indicator 18 will continue to actively reflect the state of the spring 20. For example, the number indicated by the dose indicator 18 may change to zero when delivery of a dose of medicament is complete, thereby reflecting the discharged state of the spring 20.

Description of Second Example Embodiment

A further, non-limiting, embodiment of an injection device according to the present invention is illustrated in FIGS. 4-19B.

Figure 6:
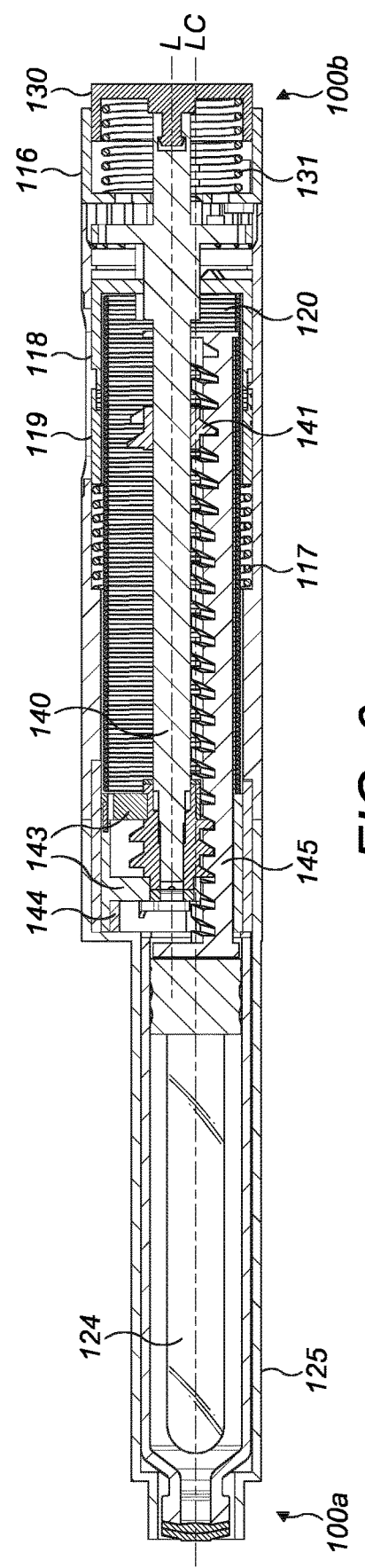
FIG. 6 is a cross-sectional view of the injection device of FIG. 4.

Referring to FIGS. 4-6, the injection device 100 includes a housing 112, a dose selector 116, a dose button 130 and dose button spring 131, a units wheel 118, a tens wheel 119, a dose indicator spring 117, a drive shaft 140, a drive spring 120, a dose limit nut 141, a worm gear 142, a worm gear support 143 and a worm gear rotational lock 144, all located concentrically about a common longitudinal axis L. The axis L extends between a front end 100a and a rear end 100b of the injection device 100.

The injection device 100 has a medicament cartridge 124 supported in a cartridge holder 125 at the front end 100a of the injection device 100. The cartridge 124 is sealed by an axially-moveable cartridge stopper 126 at its rear end. The cartridge and cartridge holder are located concentrically about a second longitudinal axis Lc, such that the cartridge is offset from the main housing 112, with L and Lc offset from one another as shown in FIG. 6.

Figure 7A:
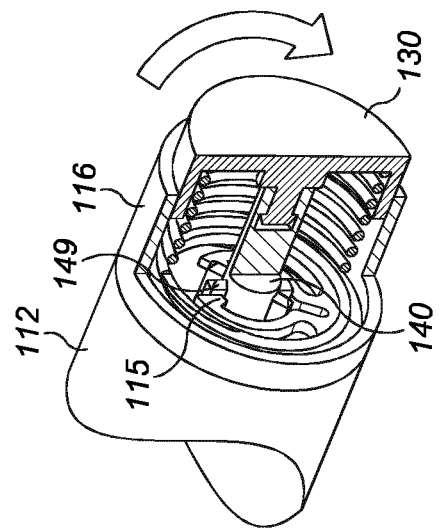
Figure 8:
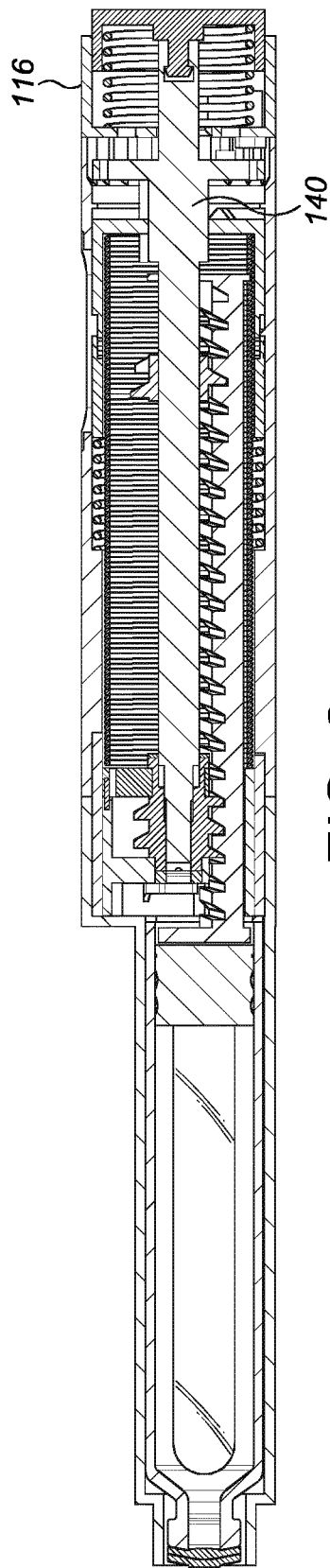
FIGS. 8, 8A and 8B illustrate decrementing the dose.
Figure 8B:
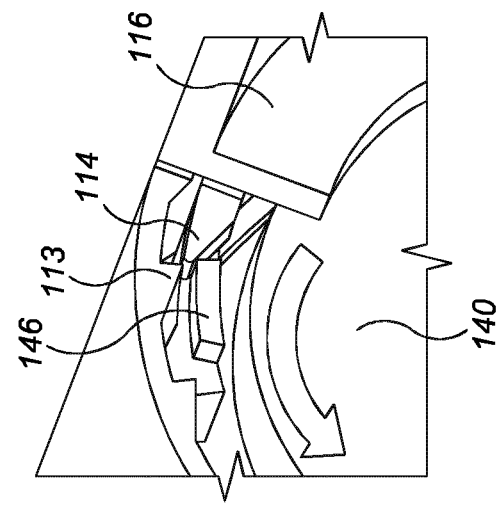

The dose button 130 is biased rearwardly by the dose button spring 131. The dose selector 116 is provided at the rear end 100b of the injection device 100 and is arranged to permit the selection of a desired dose of medicament for delivery from the medicament cartridge 124 into an injection site. The dose selector 116 is axially constrained with respect to the housing 112 but is rotatable with respect thereto, about axis L. The dose selector 116 is rotationally coupled to the drive shaft 140 via pawl features 115, visible in FIG. 7A, which engage splines 149 on the drive shaft 140. The housing 112 is provided with teeth 113 (visible in FIG. 7A) on an inside surface thereof for engaging ratchet arms 146 on the drive shaft 140. Tabs 114 on the dose selector 116 are capable of depressing the drive shaft ratchet arms 146 when required, as shown in FIG. 8B. The housing 112 is also provided with ramp features 111 (visible in FIG. 12A) which facilitate disengagement of the ratchet arms 146 from the inside surface of the housing 112 when required.

A dose indicator is disposed within the housing 112 and displays reference indicia, such as numbers or symbols, to indicate the level of dose selected by the dose selector 116. The housing 112 includes an aperture 112a through which the dose indicator is visible. The dose indicator comprises the units wheel 118 for displaying units and the tens wheel 119 for displaying tens. The units wheel 118 is selectively engageable with the tens wheel to increment the tens wheel each time the units wheel moves through units 0 to 9. The units wheel 118 is rotationally coupled to the drive shaft 140.

As with the first embodiment, described with reference to FIGS. 1-3, biasing means in the form of dose indicator spring 117 biases the units wheel 118 and tens wheel 119 axially rearwardly in the housing.

The housing 112 has features on an inside surface thereof for engaging with the units wheel 118 and the tens wheel 119.

An internal surface of the housing 112 is provided with a tens housing feature 108 selectively engageable with the tens wheel 119 to prevent rotation thereof. The tens housing feature comprises one or more axially forwardly extending formations 108 which may be equally spaced around the internal circumference of the housing 112. The formations 108 engage with corresponding axially rearwardly extending formations 119b at the rear of the tens wheel 119. The tens housing feature formations 108 and the tens wheel formations 119b may be teeth, notches, castellations or any other shaped formations that, when engaged together, prevent relative rotation between the tens wheel 119 and the housing 112.

An internal surface of the housing 112 is provided with a units housing feature 107 capable of moving the units wheel axially-forward against said biasing means 117. The units housing feature is an axially forwardly extending formation 107 having a cam surface which can engage with an axially rearwardly extending formation 118b on the units wheel 118 in order to push the units wheel 118 axially forwards.

Teeth 118a on the front end of the units wheel 118 are engageable with correspondingly shaped teeth 119a at the rear end of the tens wheel 119. On the tens wheel 119, the teeth 119a (for engaging the units wheel) and the tens wheel formations 119b (for engaging the housing) may be concentrically arranged around the longitudinal axis of the injection device, with the teeth 119a radially inward of the formations 119b.

The drive spring 120 is a torsion spring which is fixed at one end with respect to the housing 112 and rotationally coupled at its other end to the drive shaft 140 via the units wheel 118.

A worm gear arrangement is provided which comprises a worm gear 142 meshed with a toothed plunger rack 145 located within the housing 112. During dose delivery, the worm gear 142 drives the plunger rack 145 forward which, in turn, pushes against the cartridge stopper 126 to deliver a dose of medicament. A splined clutch 150 at the forward end of the drive shaft 140 enables the worm gear 142 and drive shaft 140 to be splined together during dose delivery but not during dose setting and this will be described in more detail later. In FIG. 6, the worm gear rotational lock 144 is engaged in the forward end of the worm gear 142, preventing rotation thereof. The worm gear rotational lock 144 is capable of being pushed axially forward by the drive shaft 140 in order to disengage the lock from the worm gear 142.

The dose limit nut 141 is keyed to the drive shaft 140 so that they are rotationally coupled but not axially coupled. The dose limit nut 141 is engaged with the teeth of the plunger rack 145 and can travel axially forward and backward along the plunger rack 145 as the dose is incremented or decremented respectively. The axial range within which the dose limit nut 141 can travel along the plunger rack 145 is determined by dose limit nut endstop features 141a, 141b which can engage features on the plunger rack thread to serve as endstops for the travel of the dose limit nut 141. FIG. 5A shows the maximum dose limit nut endstop feature 141a and the minimum dose limit nut endstop feature 141b in more detail. Endstops 141a, 141b are able to engage features 147, 148 respectively on the plunger rack 145 (FIG. 5B). These features 147, 148 are preferably changes in the depth of or formations on the plunger rack thread, past which the dose limit nut 141 cannot travel. During dose delivery, the dose limit nut 141 rotates about axis L with the drive shaft 140 to which it is keyed, but it does not move axially with respect to the plunger rack 145 with which it is engaged, thus always keeping the dose limit nut 141 within the range defined by the max/min dose endstops.

The operation of the respective features of the injection device 100 will now be described in more detail below.

Dose Setting—Incrementing the Dose

Figure 7:
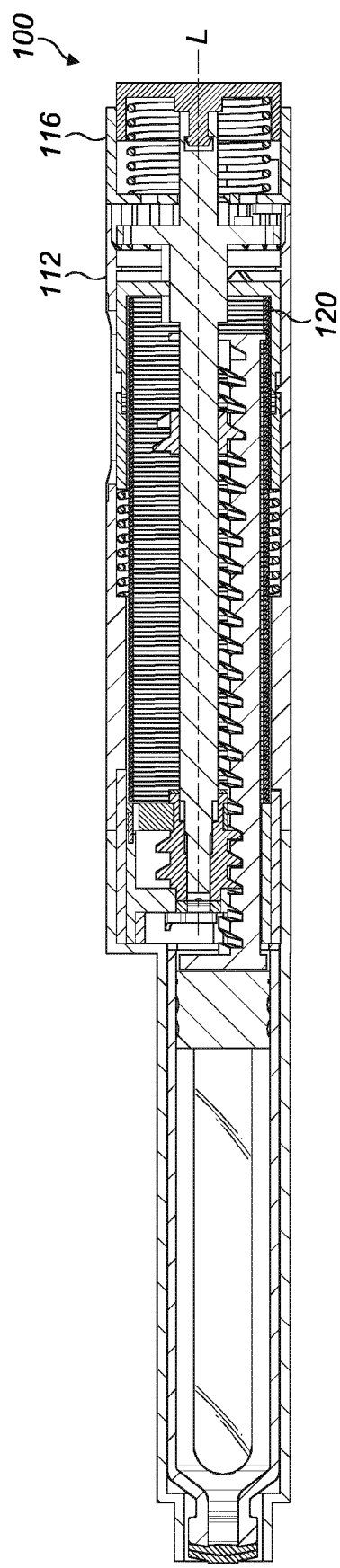
FIGS. 7 and 7A-7C illustrate incrementing the dose.
Figure 7C:
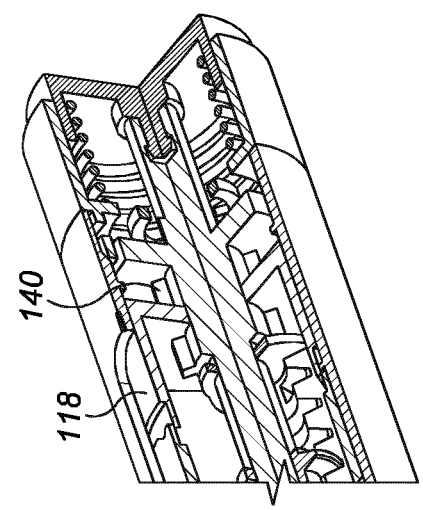

With the injection device 100 in the configuration shown in FIG. 7, the user grips the dose selector 116 and rotates it clockwise about axis L, with respect to the housing 112, in order to increment the dose and charge the drive spring 120. As the dose selector 116 is turned clockwise, the pawl features 115 engaging the splines 149 on the drive shaft 140 cause the drive shaft 140 to also be driven clockwise, as shown in FIG. 7A.

Figure 7B:
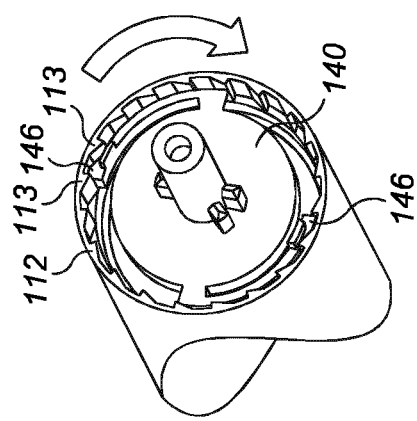

While the dose is being incremented, the ratchet arms 146 on the drive shaft 140 engage with the teeth 113 on the inside surface of the housing 112 to prevent un-winding by the drive spring 120, as shown in FIG. 7B.

As shown in FIG. 7C, the drive shaft 140 is splined to the units wheel 118 which charges or torques up the drive spring 120. In other words, torque is transferred from the dose selector 116 to the drive spring 120 directly through the dose indicator, i.e. the units wheel 118.

Dose Setting—Decrementing the Dose

Figure 8A:
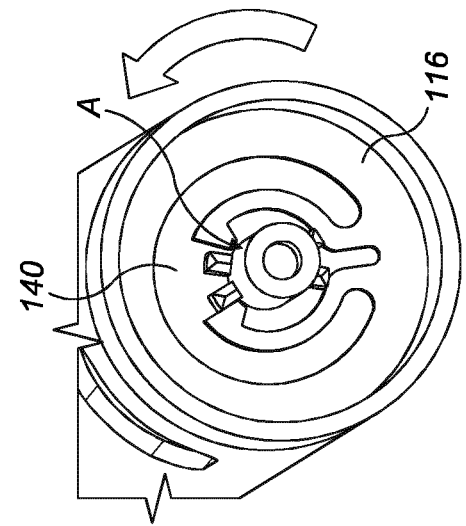

When it is desired to decrement the selected dose, the dose selector 116 is turned anti-clockwise. As shown in FIG. 8A, as the dose selector 116 is turned anti-clockwise, there is a small amount of backlash at point A such that the dose selector 116 can rotate slightly with respect to the drive shaft 140. This small relative movement is sufficient to allow the tabs 114 on the dose selector 116 to depress the drive shaft ratchet arms 146 so that they can click past the housing teeth 113, allowing the drive spring to unwind slightly before the ratchet arms 146 catch again on the next housing tooth 113. This is represented in FIG. 8B. Each decrement preferably equates to 1 IU ("international unit") of medicament.

Dose Setting—Maximum/Minimum Dose

Figure 9:
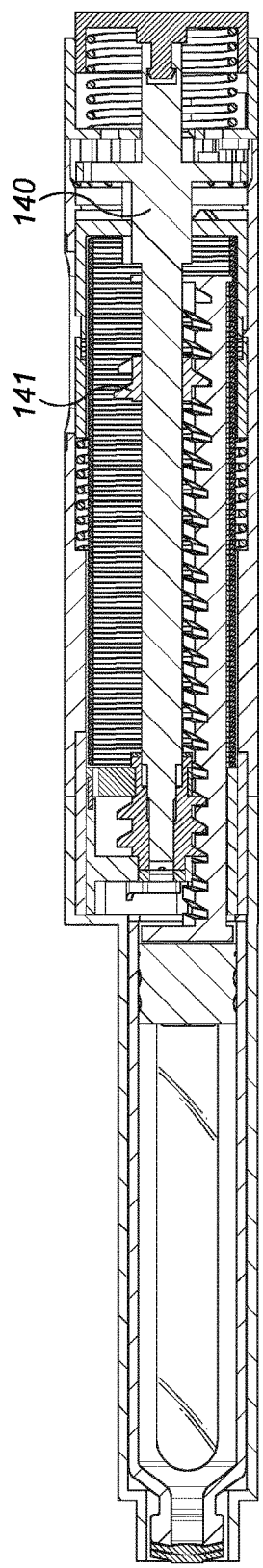
FIGS. 9, and 9A-9D illustrate maximum/minimum dose limiting.
Figure 9C:
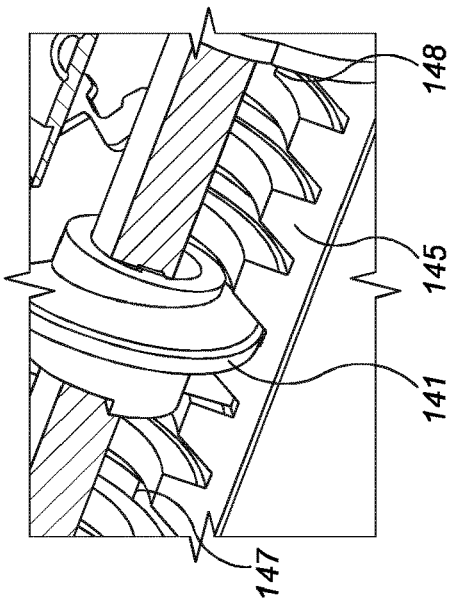
Figure 9B:
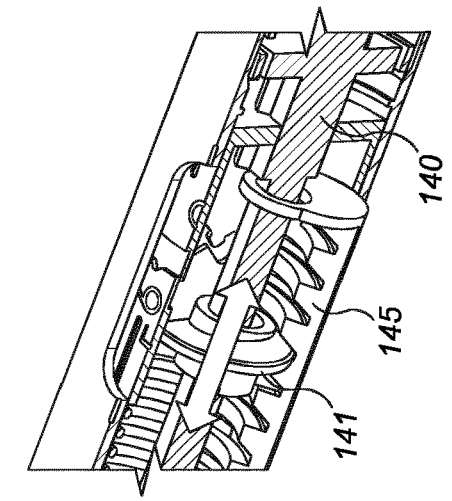
Figure 9A:
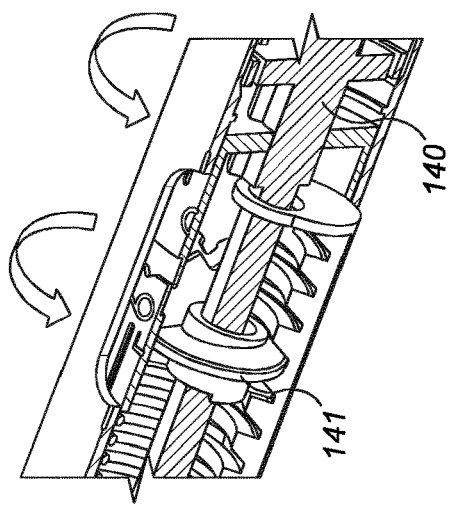
Figure 9D:
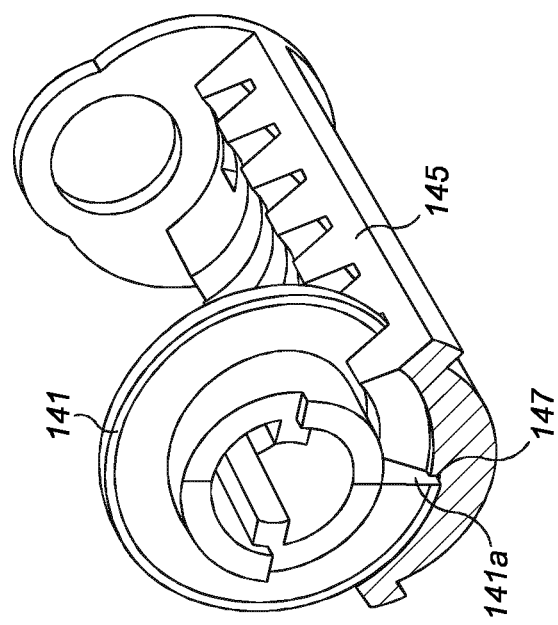

As the drive shaft 140 is rotated during dose setting, the dose limit nut 141, which is keyed to the drive shaft 140, is also rotated (FIG. 9A). The dose limit nut 141 travels forwards when incrementing the dose and rearwards when decrementing the dose (FIG. 9B). The dose limit nut 141 is engaged in the thread of the plunger rack 145. Endstop features 147, 148 are located on the plunger rack 145, past which the dose limit nut 141 cannot travel (FIG. 9C). These endstop features 147, 148 may be changes in the depth of the thread. As shown in FIG. 9D, when the dose limit nut 141 rotates into a position wherein the dose limit nut endstop feature 141a engages feature 147 on the plunger rack 145, a rotary endstop occurs, preventing further rotation of the dose limit nut 141 so that a dose of medicament greater than the desired maximum dose of medicament cannot be set. Limiting the travel of the dose limit nut 141 sets the maximum and minimum doses of medicament that can be set during dose setting, preferably 100 IU and 0 IU respectively.

Dose Setting—Over Torque

Figure 10:
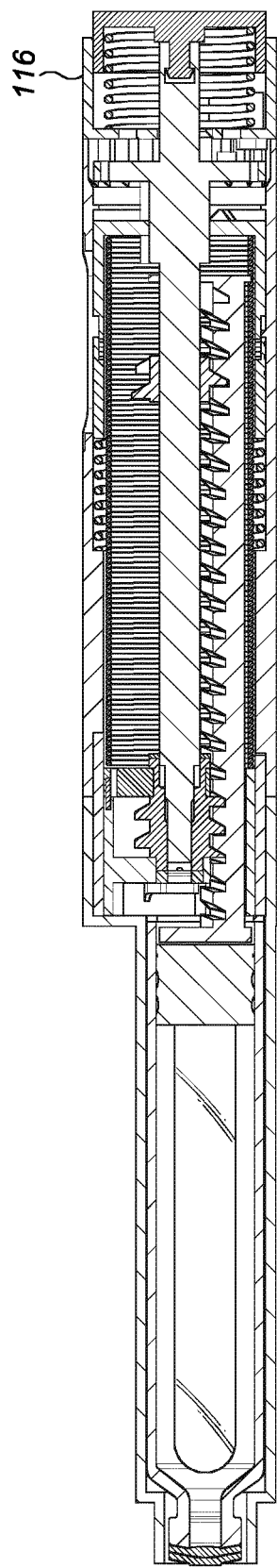
FIGS. 10 and 10a illustrate over-torque protection.
Figure 10A:
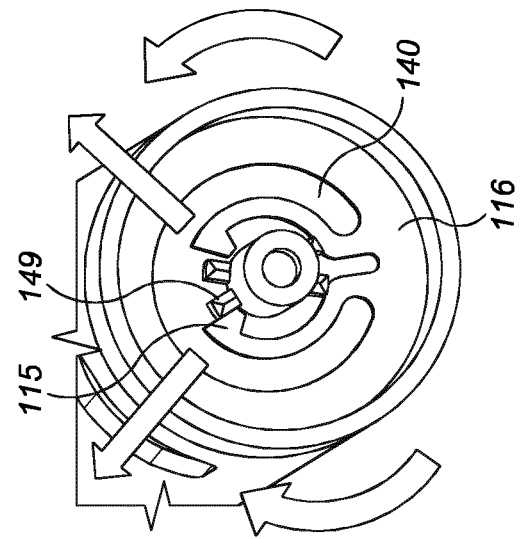

As shown in FIG. 10A, in the event the user applies too much force (over torque) to the dose selector 116 in either rotational direction, the dose selector pawl features 115 will flex radially outwardly to allow them to skip past splines 149 on the drive shaft 140. Preferably the interfacing surface areas of the pawl features 115 and/or splines 149 act as a cam lever, preferably having a matching angle and/or a defined static and dynamic surface friction at the interface surface. The over-torque for flexing out the dose pawl features 115 to skip past spline 149 is preferably at least 10% higher than the torque required for dialing up (incrementing) or dialing down (decrementing) the dose indicator 18, 118. The dialing up torque can be 30 to 80 Nmm, preferably less than 60 Nmm, more preferably 30 to 50 Nmm. The dialing down torque can be 20 to 60 Nmm, preferably less than 50 Nmm, more preferably 30 to 40 Nmm. The over-torque in the dialing up direction may be different to the over-torque in dialing down direction. The outward flexing force and/or strength of one flexible pawl arm 115 could be lower compared to a second flexible pawl arm.

Figure 16:
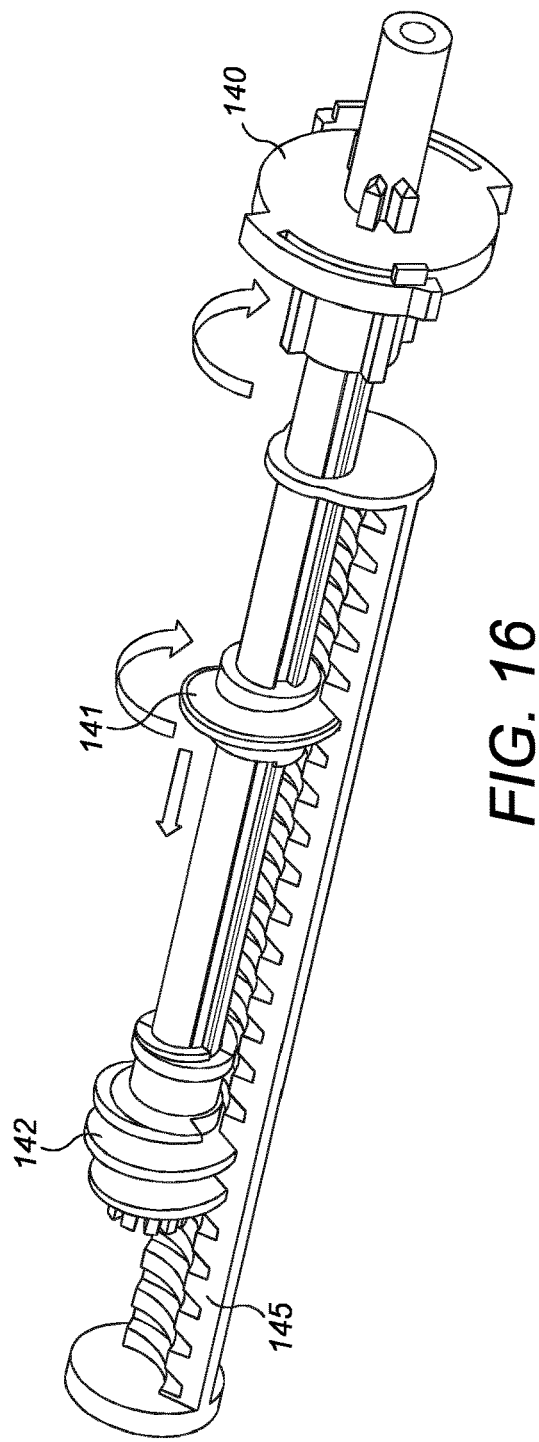
FIG. 16 summarises schematically the mechanical motion of the drive shaft 140, dose limit nut 141, worm gear 142 and plunger rack 145 during dose setting (incrementing the dose)

FIG. 16 summarises schematically the mechanical motion of the drive shaft 140, dose limit nut 141, worm gear 142 and plunger rack 145 during dose setting (incrementing the dose). The drive shaft 140 rotates clockwise. The dose limit nut 141 rotates clockwise and advances forwards with respect to the plunger rack 145.

Dose Delivery

Figure 11:
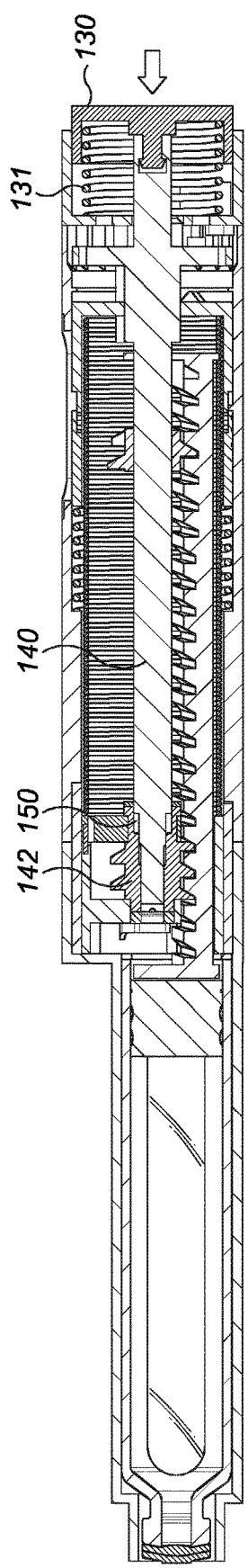
Figure 11A:
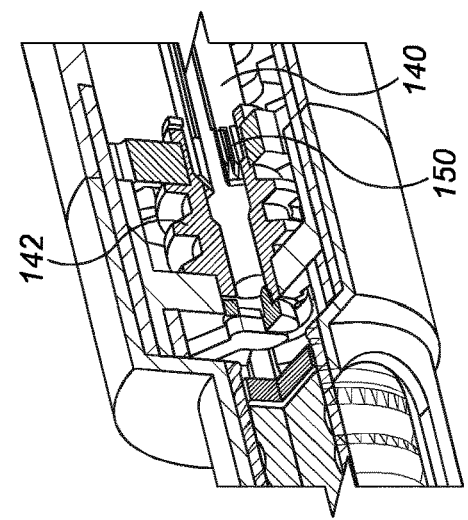
Figure 11B:
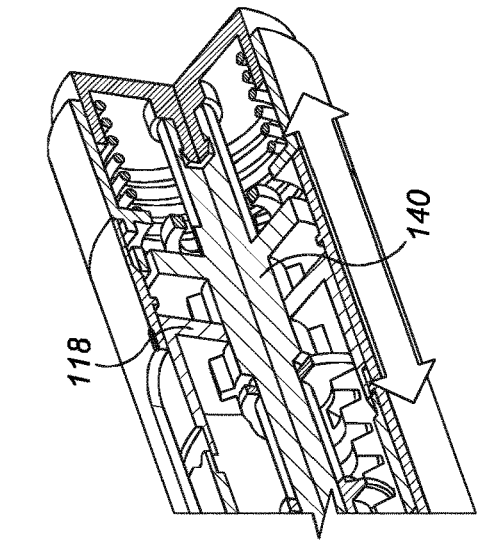

To initiate dose delivery, the user presses the dose button 130 against the bias of the dose button spring 131 as shown in FIG. 11A. This pushes the drive shaft 140 axially forwards. Although the drive shaft 140 is splined to the units wheel 118, it is free to slide axially with respect thereto (FIG. 11B).

Figure 11C:
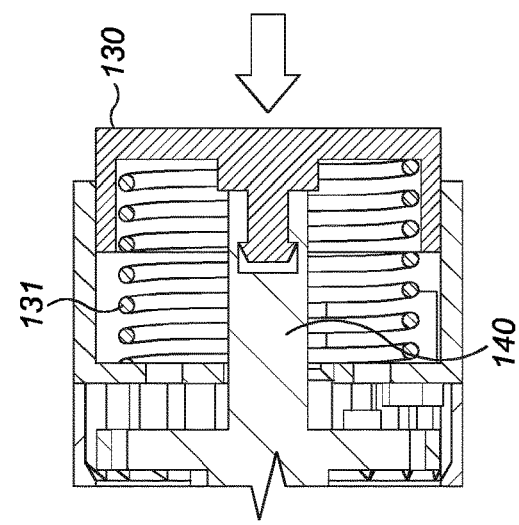
Figure 15:
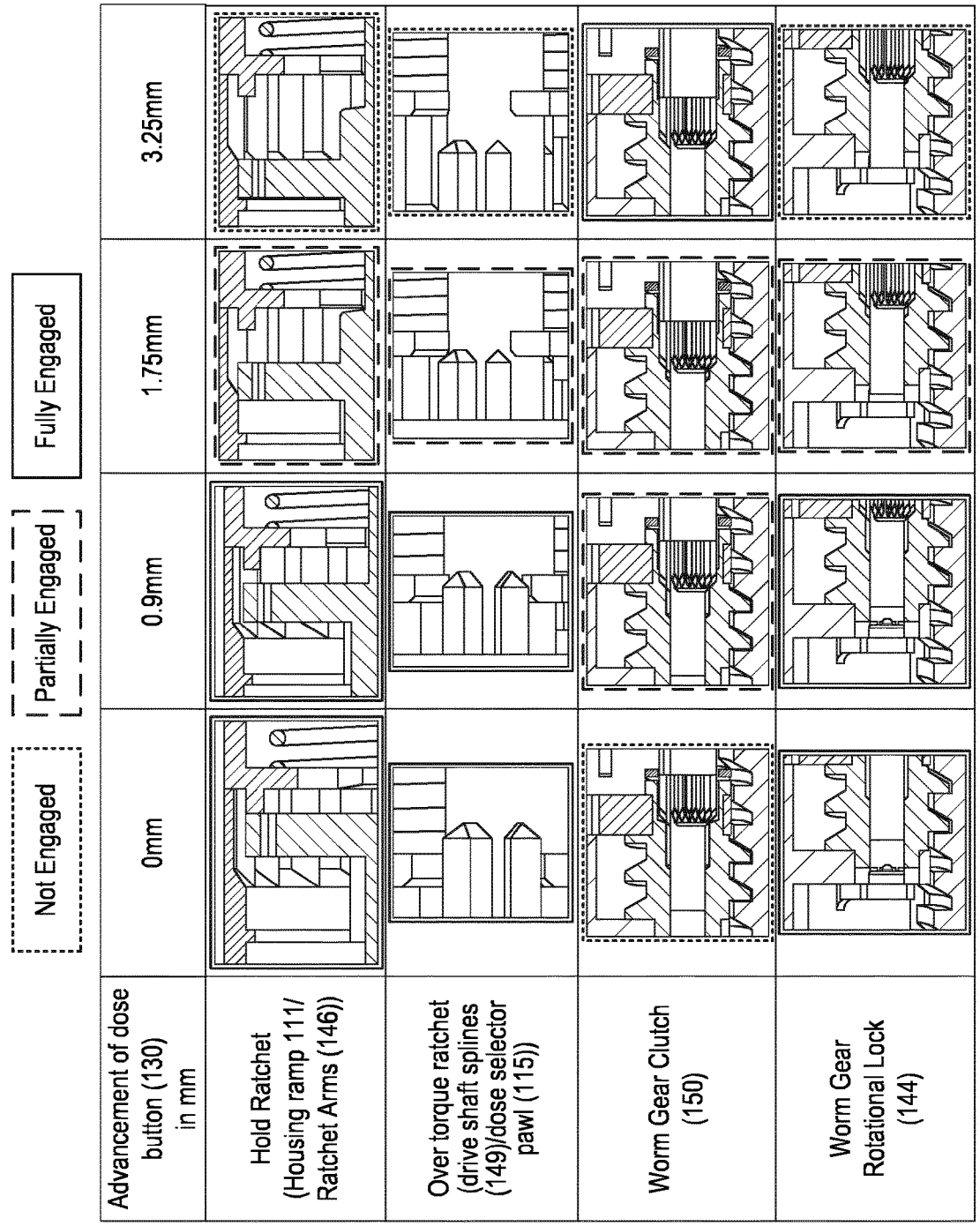
FIG. 15 is a diagrammatic summary of the key engagement points of the components of the injection device of FIG. 4, at four stages of dose delivery.

As the drive shaft 140 advances, at its forward end, the splined clutch 150 between the drive shaft and the worm gear 142 engages (FIG. 11C, FIG. 15—Worm Gear Clutch 150). Preferably the drive element, in particular the worm gear 142 and the drive shaft 140 engage after 0.5 mm to 1.5 mm advancement of the dose button 130, more preferably after 0.8 mm to 1.2 mm advancement of the dose button 130. Once the clutch 150 has started to engage, the ratchet arms 146 on the drive shaft 140 begin to disengage from the inside surface of the housing 112 aided by ramp features 111 (FIG. 12A, FIG. 15—Hold Ratchet). Preferably the hold ratchet, in particular the ratchet arms 146 on the drive shaft 140 start to disengage from the structured, in particular toothed surface of the housing 112 after 1.5 mm to 2.5 mm advancement of the dose button 130, more preferably after 1.6 mm to 1.9 mm advancement of the dose button 130. Also, as the drive shaft 140 moves forward, the splines 149 coupling the drive shaft 140 to the dose selector 116 disengage (FIG. 12B, FIG. 15—Over torque ratchet). Preferably the over torque ratchet, in particular the drive shaft splines 149 on the drive shaft 140 start to disengage from the dose selector pawls 115 after 1.5 mm to 3.5 mm of advancement of the dose button 130, more preferably after 2 mm to 3 mm advancement of the dose button 130. The dose indicator and drive shaft 140 are now free to rotate about longitudinal axis L.

The drive spring 120 drives the units wheel 118 to rotate about longitudinal axis L. The units wheel 118 drives the drive shaft 140 which drives the worm gear 142.

Figure 17:
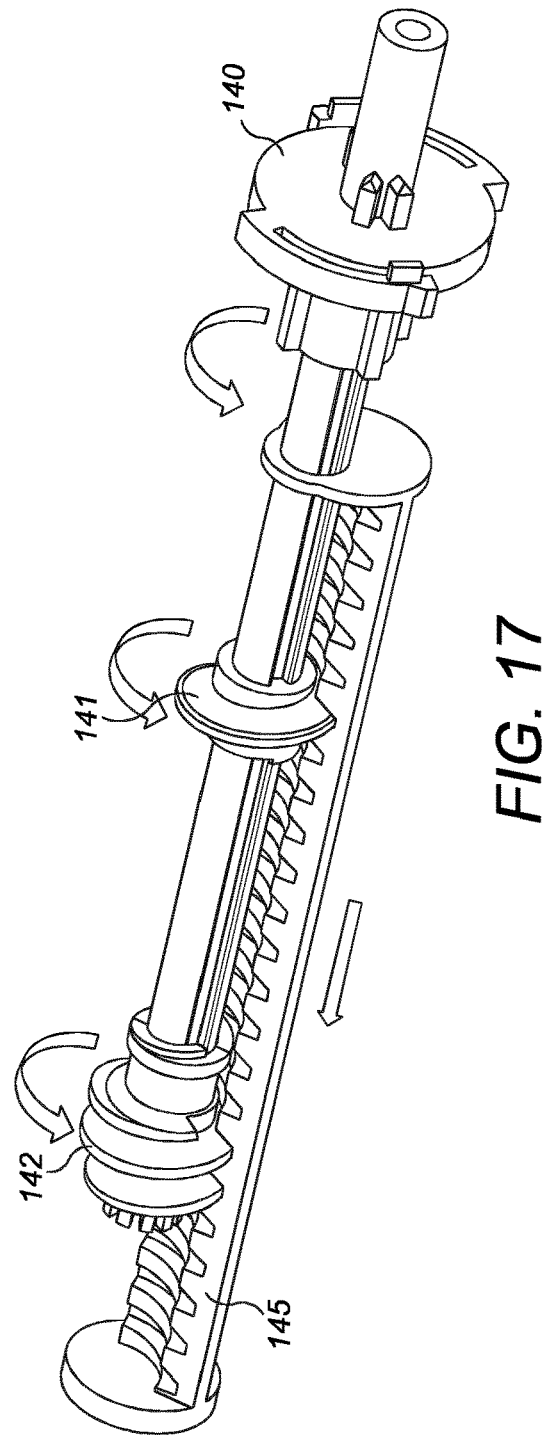
FIG. 17 summarises schematically the mechanical motion of the drive shaft 140, dose limit nut 141, worm gear 142 and plunger rack 145 during dose delivery.

FIG. 17 summarises schematically the mechanical motion of the drive shaft 140, dose limit nut 141, worm gear 142 and plunger rack 145 during dose delivery. The drive shaft 140, dose limit nut 141 and worm gear 142 all rotate anti-clockwise. Only the plunger rack 145 advances forwards. During dose delivery, the dose limit nut 141 rotates with the drive shaft 140 but does not move axially with the plunger rack 145. The dose limit nut 141 and the drive worm gear 142 preferably have the same thread pitch.

The worm gear 142 actuates the plunger rack 145 to move axially forwards causing the cartridge stopper 126 to be driven into the cartridge in order to expel medicament thus delivering the selected dose.

When the dose button 130 is released, the dose button spring 131 returns the dose button 130 and drive shaft 140 to their original starting positions. This axially rearward movement disengages the worm gear clutch 150 and re-engages the drive shaft ratchet arms 146 with the housing 112 thereby stopping dose delivery.

Dose Delivery—Haptic Feedback

Figure 13:
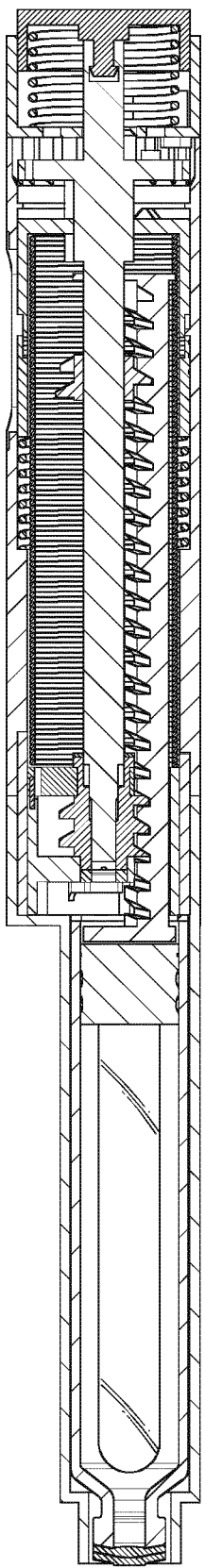
FIGS. 13, 13A and 13B illustrate a haptic feedback feature.
Figures 13A, 13B:
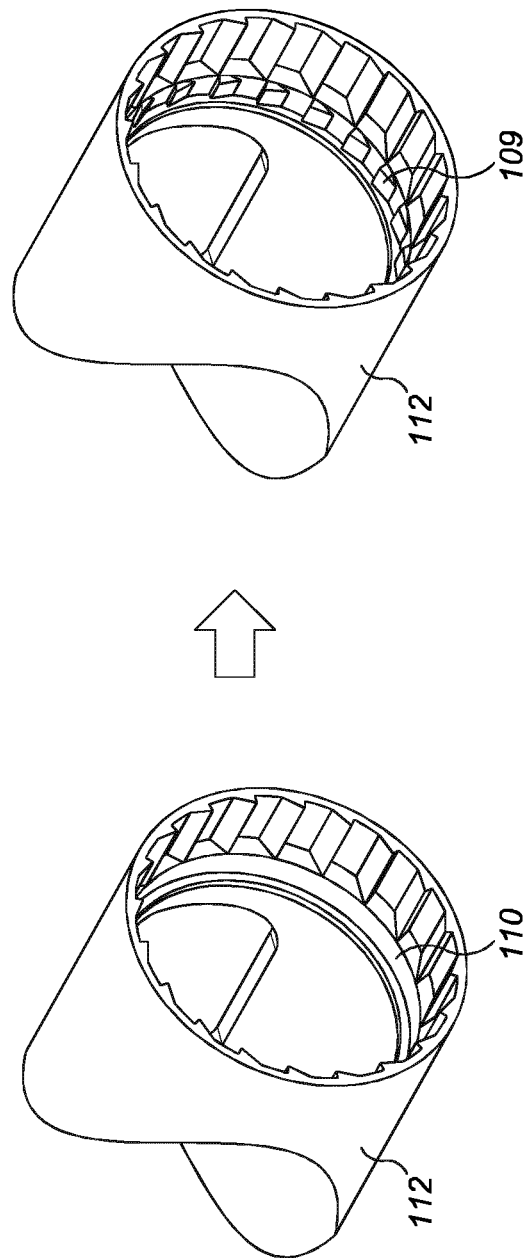

During dose delivery, the drive shaft ratchet arms 146 run (rotationally) on a relatively smooth track 110 on the inside surface of the housing 112 (FIG. 13A). Optionally, this track could be modified to include ridges 109 which would provide audible/haptic feedback to the user during dose delivery (FIG. 13B). The ridges 109 are conveniently placed relatively close to the user's fingers.

Last Dose Protection

When the medicament cartridge 124 is relatively empty, after several doses have already been delivered therefrom, it is undesirable for the user to be able to select a dose that is larger than the available quantity of medicament remaining. Last dose protection is provided to deal with this situation. Conveniently, the last dose protection is provided by the same feature as the max/min dose limiting i.e. the dose limit nut 141.

As shown in FIG. 14, after several doses have been delivered, the plunger rack 145 and dose limit nut 141 have advanced axially forwards such that the dose limit nut 141 is approaching the worm gear 142. When there is less than a predetermined amount (e.g. 100 IU) of medicament available, the worm gear 142 serves as an endstop, stopping the dose limit nut 141 from moving further forwards and before the maximum dose limit feature 147 on the plunger rack 145 is reached (FIG. 14A). Preferably, it is the dose limit nut endstop feature for maximum dose limiting 141a which engages the worm gear 142. If the user tries to increment the dose further, torque is transmitted through the dose limit nut 141 into the worm gear 142, the torque being reacted to by the worm gear rotational lock 144 (FIG. 14B). As such, the worm gear 142 is unable to rotate due to rotational engagement with the rotational lock 144.

Figure 14C:
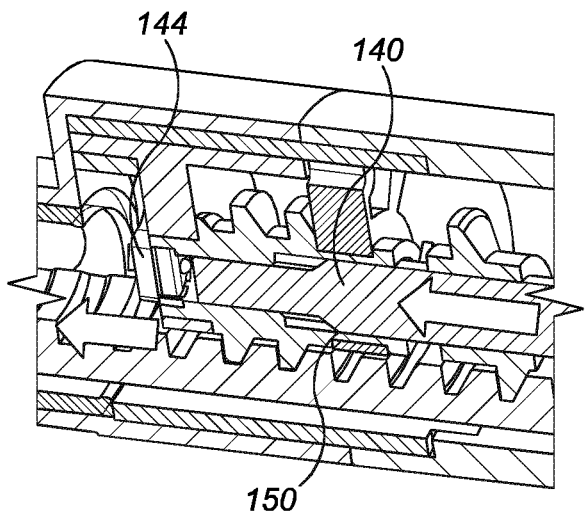
Figure 14D:
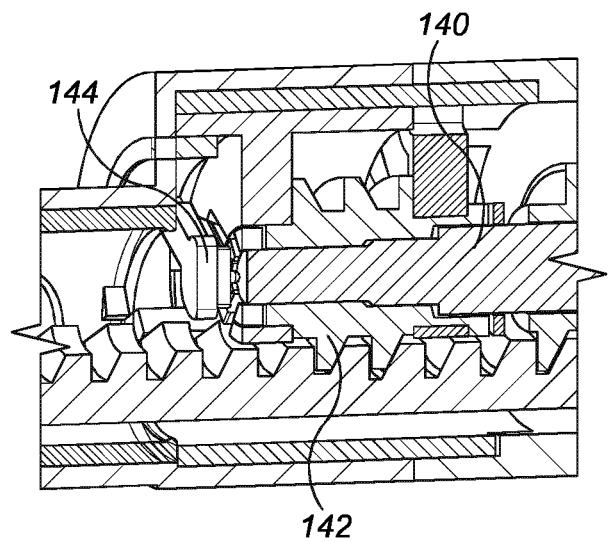
Figure 14E:
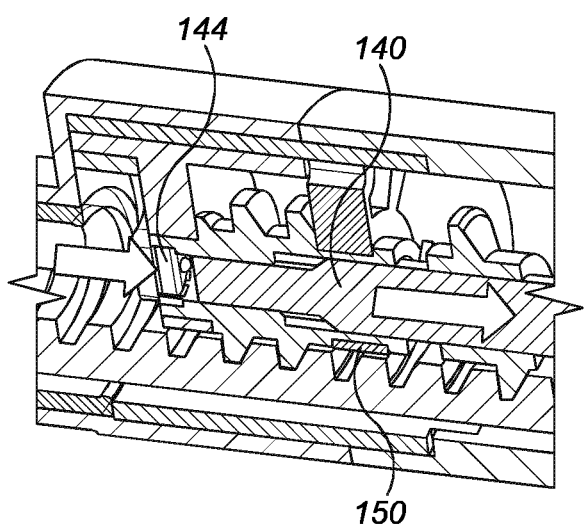

During dose delivery, when the drive shaft 140 is moved axially forwards, the worm gear clutch 150 is engaged before the worm gear rotational lock 144 is disengaged (FIG. 14C). The axially-forward movement of the drive shaft 140 causes its forward end to push the worm gear rotational lock 144 out of the front of the worm gear 142. With the worm gear rotational lock 144 disengaged, the worm gear 142 is free to rotate, driven by the drive shaft 140 (FIG. 14D). Once dose delivery is finished, the drive shaft 140 moves rearwardly. The worm gear rotational lock 144 re-engages, before the worm gear clutch 150 is disengaged (FIG. 14E).

FIG. 15 is a diagrammatic summary of the key engagement points of the injection device components, at four stages of dose delivery.

Dose Display

Figure 18:
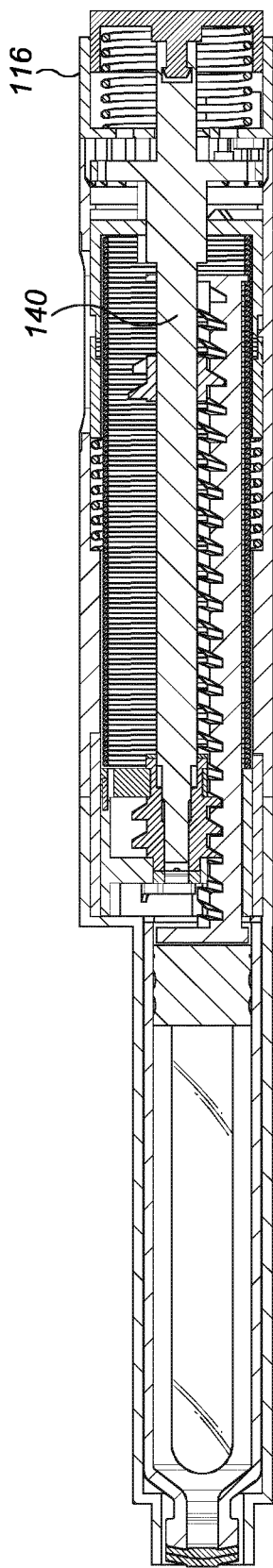
FIGS. 18, 18a and 18B show how the units wheel is incremented.
Figure 18B:
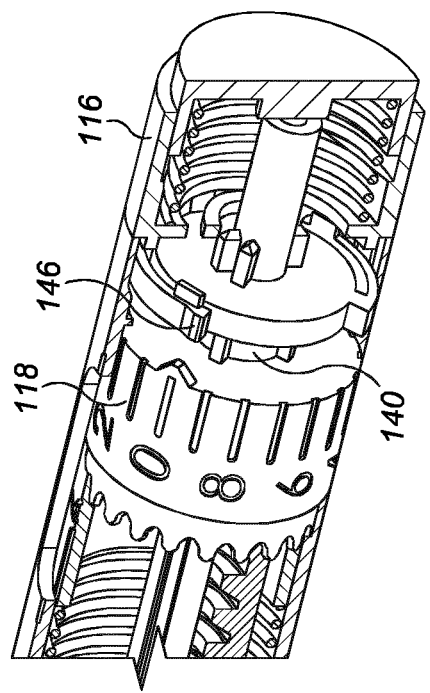
Figure 18A:
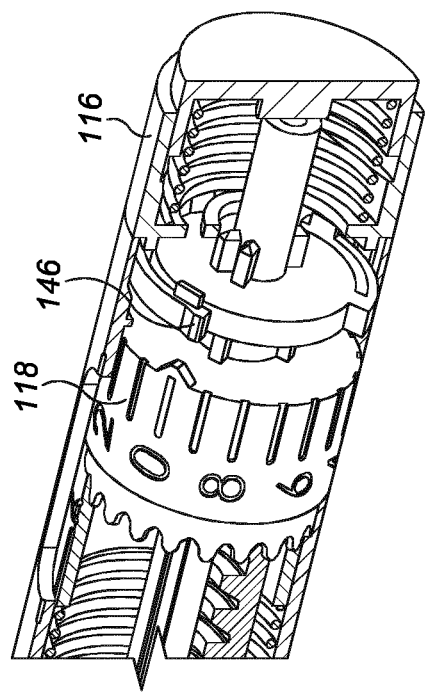
Figure 20:
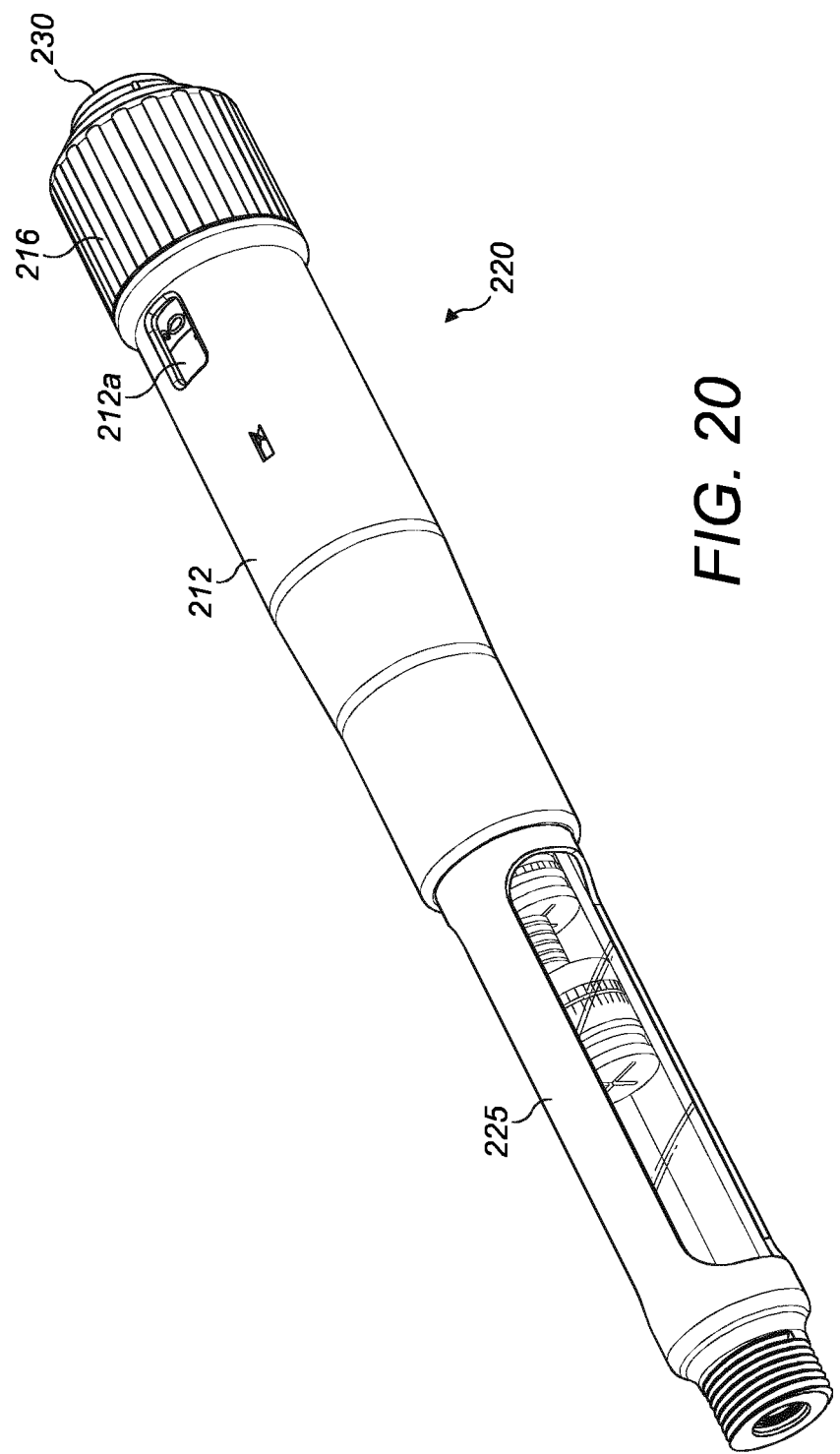
FIG. 20 is a perspective view of another embodiment of the injection device.

As already described above, during dose selection the user rotates the dose selector 116 which also drives the drive shaft 140 around. Ratchet arms 146 interact with teeth 113 in the housing 112 to prevent unwinding (FIG. 18A). The drive shaft 140 is splined to the units wheel 118 which, as it turns, increments the displayed unit (FIG. 18B).

The units wheel 118 and tens wheel 119 are biased rearwardly by dose indicator spring 117. Twice per revolution of the units wheel 118, the units wheel 118 is moved axially forwards by the cam surface of the units housing feature 107 engaging with the formation 118b on the units wheel 118. This axially forward movement causes the teeth 118a of the units wheel 118 to engage with the teeth 119a of the tens wheel 119 (FIG. 19A). Continued forward axial movement of the units wheel 118 pushes the formations 119b of the tens wheel 119 away from the tens housing feature 108, so that the tens wheel 119 is free to rotate with respect to the housing 112, allowing the tens wheel 119 to be driven around by the units wheel 118 by one increment (FIG. 19B).

In a preferred embodiment, the selectable and settable dose range is 1 to 100 IU, with a minimum dose setting of 1 IU, wherein per 360 degree rotation of the dose selector 116, 20 to 30 IU may be set. As the units wheel 118 and tens wheel 119 arrangement permits indication of the set IU dose by two digits, a much larger font size for the indicated dose number is usable, thus the arrangement affords better readability of the set dose and usability of the injection device 10, 100.

As with the first embodiment, described with reference to FIGS. 1-3, the drive spring 120 is coupled to the units wheel 118 (via the drive shaft 140 splined to the units wheel 118) such that a charging force can be transferred from the dose selector 116 to the spring 120 via the units wheel 118 to increase the energy stored by the spring 120. Such a coupling is preferably achieved by locking one end of the drive spring 120 to the units wheel 118 and winding the drive spring 120 when the units wheel 118 is turned during dose selection. The other end of the drive spring 120 is fixed against rotational movement, preferably being fixed to a part of the housing 112. By coupling the spring 120 to the units wheel 118, a more accurate dose indication may be achieved. When the dose selector 116 is rotated by a user, the dose indicator (units wheel 118 and tens wheel 119), which is in series therewith serves a dual function of both displaying the currently selected dose and also transferring the charging force from the dose selector in order to charge the drive spring 120.

Description of Third Example Embodiment

A further, non-limiting, embodiment of an injection device according to the present invention is illustrated in FIGS. 20-40.

Referring to FIGS. 20-24, the injection device 200 includes a housing 212, a dose selector 216, a dose button 230 and dose button spring 231, a units wheel 218, a tens wheel 219, a ratchet pawl 217, a housing top cap 221, an odometer shuttle lock 222, a drive spring 220, a drive sleeve 240, a last dose nut 241, a drive clutch 250, a drive clutch spring 251, a leadscrew nut 252, a leadscrew 253 and a thrust bearing 254, all located concentrically about a common longitudinal axis L. The axis L extends between a front end 200a and a rear end 200b of the injection device 200.

The injection device 200 has a medicament cartridge 224 supported in a cartridge holder 225 at the front end 200a of the injection device. A needle or needle hub unit (not shown) can be connected to the cartridge holder. The cartridge is sealed by an axially-moveable cartridge stopper 226 at its rear end.

The dose button 230 is biased rearwardly by the effect of the dose button spring 231 between the housing 212 and front end of the drive sleeve 240 with which the dose button 230 is axially engaged. The dose selector 216 is provided at the rear end 200b of the injection device 200 and is arranged to permit the selection of a desired dose of medicament for delivery from the medicament cartridge 224 into an injection site. The dose selector 216 is axially constrained with respect to the housing 212 but is rotatable with respect thereto, about axis L. The dose selector 216 is used to set the dose by increasing the rotational preload of the drive spring 220 which is prevented from unwinding by the ratchet pawl 217 which engages between the housing 212 and the units wheel 218.

Figure 21:
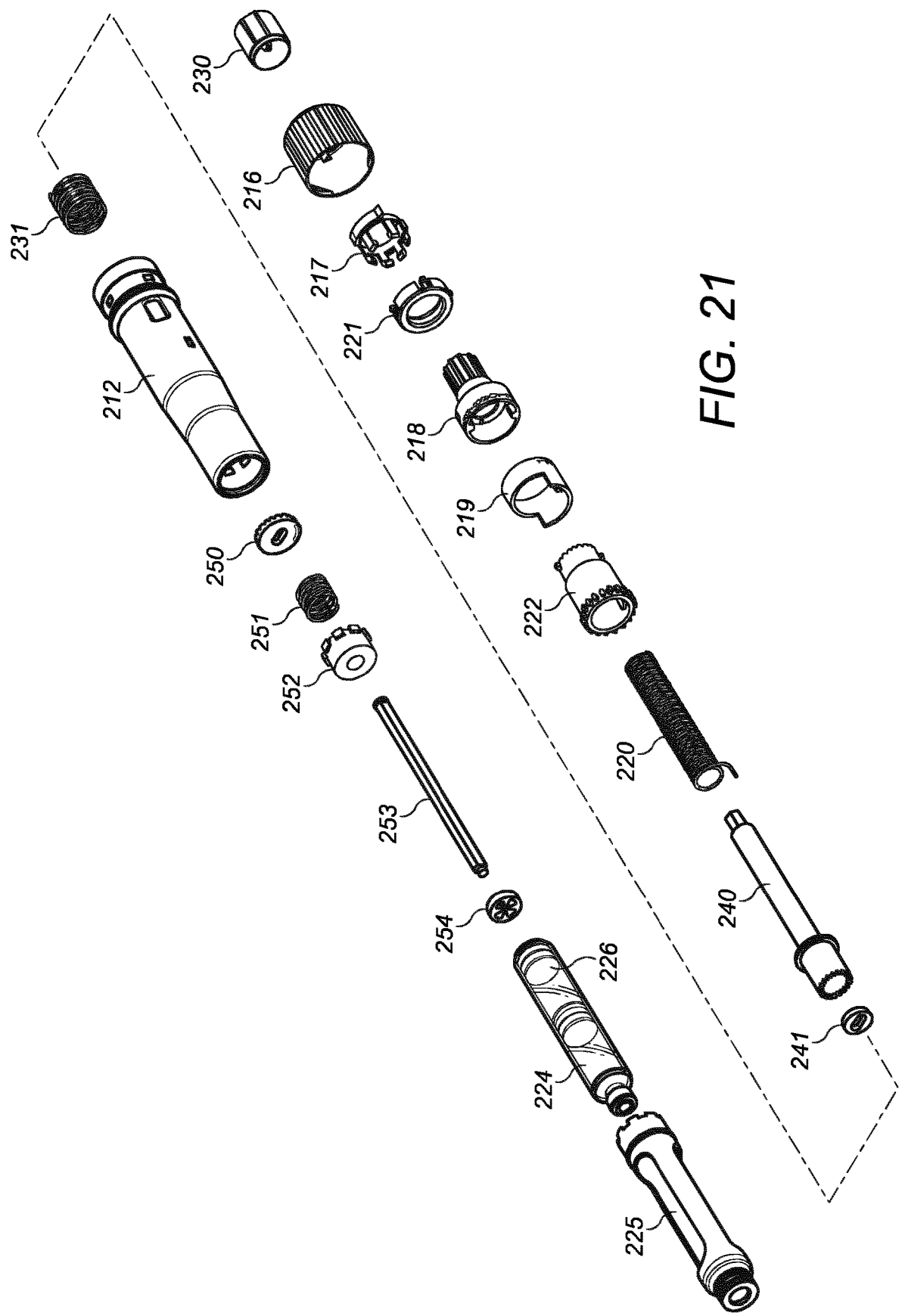
FIG. 21 is an exploded view of the injection device of FIG. 20.
Figure 21A:
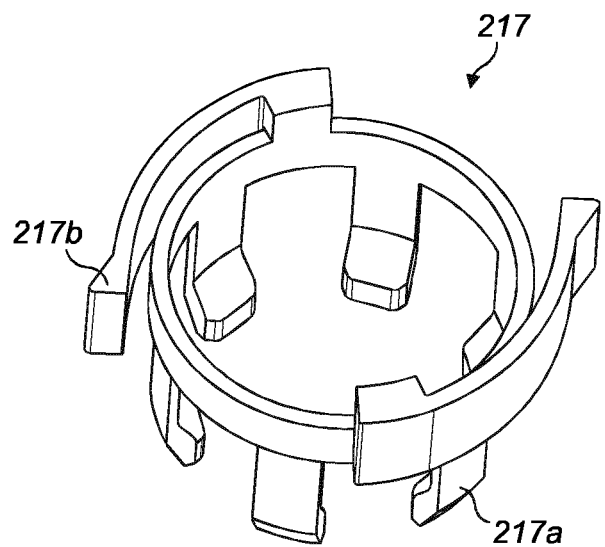
FIG. 21A is a perspective view of the ratchet pawl, drawn to a larger scale.

The ratchet pawl 217 (best seen in FIG. 21A) includes a plurality of ratchet fingers 217a which, in the assembled injection device 200, extend generally axially rearwardly to engage with the units wheel 218 as shown in FIG. 25C. The ratchet pawl 217 also includes ratchet arms 217b which, in the assembled injection device 200, engage with teeth 213 on the inside surface of the housing 212 to prevent unwinding of the drive spring 220, as shown in FIG. 25B, while the dose is being incremented.

A dose indicator is disposed within the housing 212 and displays reference indicia, such as numbers or symbols, to indicate the level of dose selected by the dose selector 216. The housing 212 includes an aperture 212a through which the dose indicator is visible. The dose indicator comprises the units wheel 218 for displaying units and the tens wheel 219 for displaying tens and the odometer shuttle lock 222. The units wheel 218 is intermittently coupled to the odometer shuttle lock 222 which is always rotationally coupled to the tens wheel 219. The tens wheel 219 has maximum and minimum dose limit features in the form of rotational endstops 271, 272 respectively, which can engage a limiting rib 290 in the housing 212 to keep the selected dose within the range defined by the maximum and minimum doses. This max/min dose limiting will be described in more detail later.

With reference to FIGS. 30-34, the dose indicator is an odometer comprising a units wheel 218, a tens wheel 219 and an odometer shuttle lock 222. The units wheel 218 has units numbers 260 around the circumference thereof, comprising two consecutive series of the numbers 0-9. Two drive dogs 261 are located 180 degrees apart on the internal surface of the forward end of the units wheel 218 and two engagement splines 262 are also located 180 degrees apart from one another. The sets of drive dogs 261 and engagement splines 262 may be rotationally offset from one another by approximately 90 degrees. In an alternative embodiment the units wheel 218 may comprise one consecutive series of the numbers 0-9 around its circumferential surface, and one drive dog 261. The units wheel 218 may comprise one or more than two engagement splines 262, the engagement splines 262 rotationally arranged to be engageable with the shuttle lock rear teeth 283. The drive dogs 261 have angled faces which, when engaging corresponding angled faces 282 on the shuttle lock 222, cause a camming action that can move the shuttle lock 222 axially.

Tens wheel 219 has tens numbers 270 around the circumference thereof, comprising a series of the numbers 0-10. The forward end of the tens wheel 219 includes maximum and minimum dose limit features 271, 272, in the form of rotary endstops which can each engage a max/min limit rib 290 on the internal surface of the housing 212. The internal surface of the tens wheel 219 includes a key 273 for engaging with the shuttle lock 222.

The shuttle lock 222 is a generally cylindrical component having a forward section of largest diameter with double-ended peripheral teeth 280 at the forward end thereof having angled faces which can alternately engage dogs 291 and engagement ribs 292 on the interior of the housing 212. The angled faces cause a camming action that can move the shuttle lock 222 axially.

In general terms, the function of the housing dogs 291, housing engagement ribs 292 and units wheel drive dogs 261 is to enable the shuttle lock 222 to move alternately between two axial positions, as will be explained in more detail later.

An axially-extending keyway 281 is provided for engaging the key 273 on the tens wheel 219 in order to rotationally lock the tens wheel 219 and shuttle lock 222 together whilst permitting axial movement therebetween. In alternative embodiments, the key may be provided on the shuttle lock 222 and the axially-extending keyway may be provided on the tens wheel 219.

The rear section of the shuttle lock 222 is of smaller diameter and includes dogs 282 at the rear end thereof, located 180 degrees apart from one another which can engage with the drive dogs 261 of the units wheel 218.

The rear surface of the shuttle lock 222 is provided with a series of axially-extending shuttle lock rear teeth 283. The number of teeth 283 corresponds with the number of units of medicament available per rotation of the units wheel 218 (in this case 20). Depending upon the relative axial positions of the units wheel 218 and the shuttle lock 222, the engagement splines 262 on the units wheel 218 can either be engaged with the shuttle lock rear teeth 283, or not engaged with the shuttle lock rear teeth 283.

Figure 34:
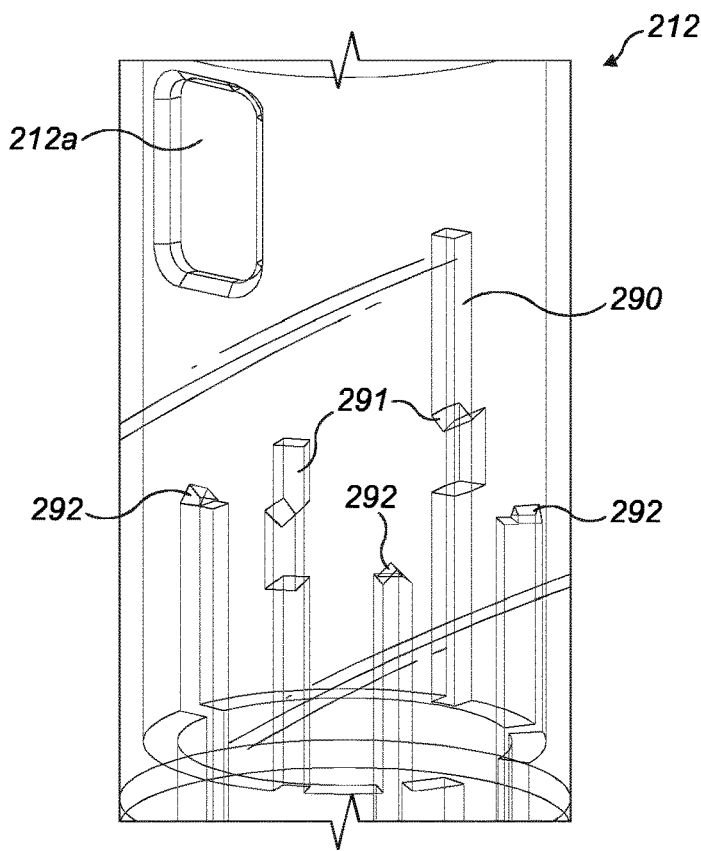
FIG. 34 is a perspective view of housing features relevant to the odometer mechanism.

FIG. 34 shows the portion of the internal surface of the housing 212 which interacts with the odometer mechanism. The aperture 212a through which the dose is displayed can be seen. The illustrated portion of the housing includes an internally-projecting max/min limit rib 290, two dogs 291 for engaging the shuttle lock 222 and three engagement ribs 292 for engaging the shuttle lock 222. FIG. 34 is shown partly in cross-section; the pointed ends of dogs 291 are at the same axial position and are located 180 degrees apart on the internal surface of the housing 212 (half of the housing 212 has been removed from FIG. 34).

As illustrated in FIG. 34, one of the dogs 291 for engaging the shuttle lock 222 may be located at one end of the max/min limit rib 290 such that both functions can be performed by the same component on the internal surface of the housing 212.

The drive spring 220 is a torsion spring which is fixed at one end with respect to the housing 212 and engaged at its other end to the units wheel 218.

Figure 21B:
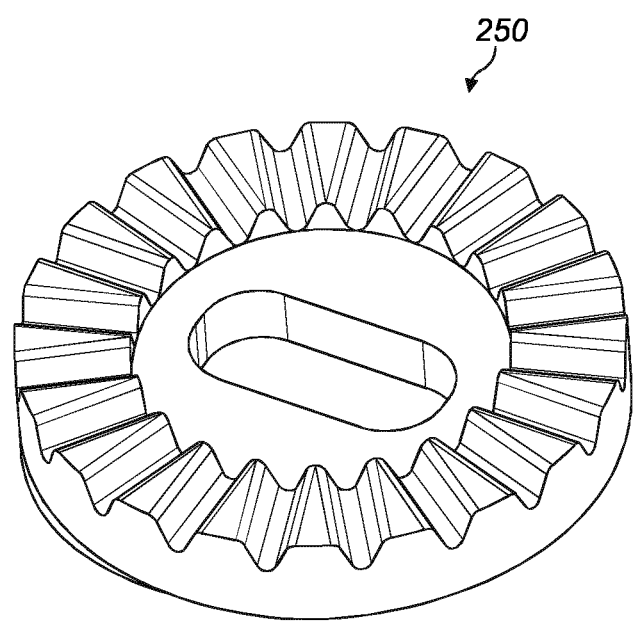
FIG. 21B is a perspective view of the drive clutch, drawn to a larger scale.
Figure 22:
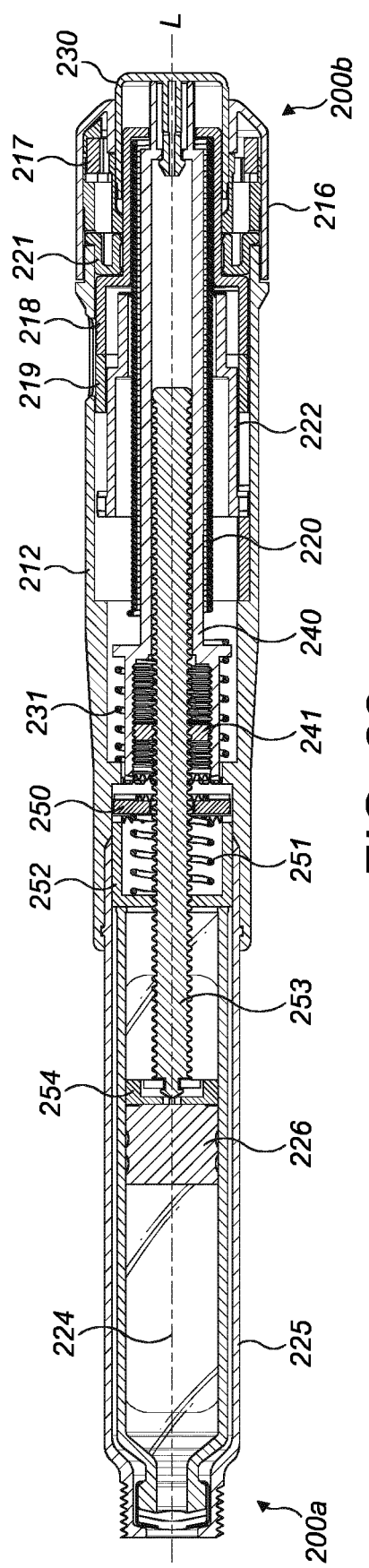
FIG. 22 is a cross-sectional view of the injection device of FIG. 20.
Figure 23:
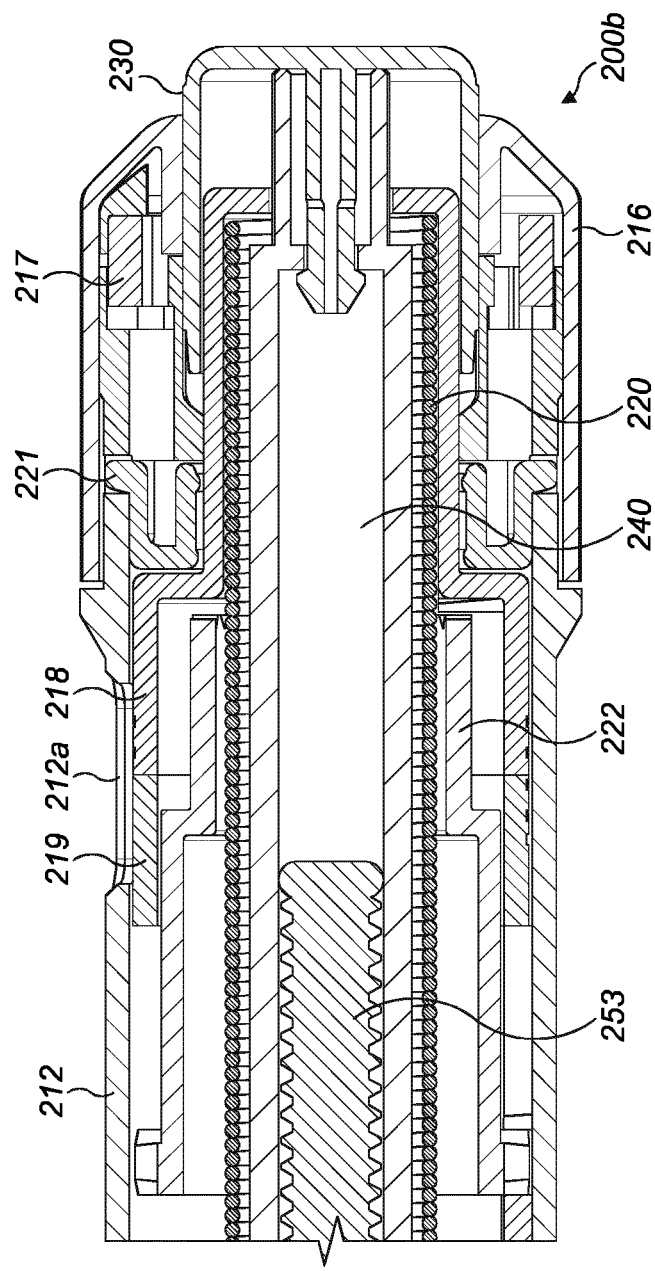
FIG. 23 is a cross-sectional view, drawn to a larger scale, of the rear end of the injection device of FIG. 20.
Figure 24:
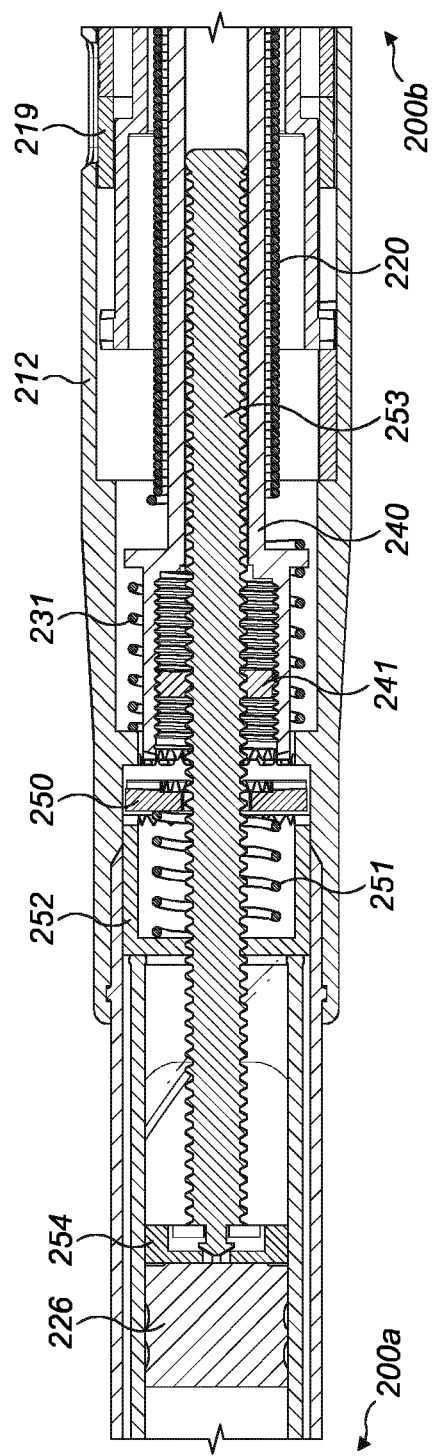
FIG. 24 is a cross-sectional view, drawn to a larger scale, of the central portion of the injection device of FIG. 20.

The drive clutch 250, best seen in FIG. 21B, is generally circular with formations (uppermost in FIG. 21B) which, in the assembled injection device 200, extend in a direction towards the rear of the device. The drive clutch spring 251 biases the medicament cartridge 224. The housing 212 is provided with forward-facing clutch engaging features 215 which, in the position shown in FIG. 25, engage the clutch 250 so that they are rotationally locked together. The clutch 250 can be disengaged from the clutch engaging features of the housing 215 by forward axial movement of the clutch 250, caused by forward movement of the drive sleeve 240. A haptic feedback arm 250a is provided on the front face of the drive clutch 250 (the underside in FIG. 21B).

The operation of the respective features of the injection device 200 will now be described in more detail below.

When the dose button 230 is depressed, firstly the drive clutch 250 is decoupled from the housing 212 and coupled to the drive sleeve 240. Secondly, the ratchet pawl 217 is decoupled from the units wheel 218. Decoupling of the ratchet pawl 217 from the units wheel 218 allows the drive spring 220 to rotate the units wheel 218 and drive sleeve 240, which are rotationally coupled together, about the longitudinal axis L.

Rotation of the drive sleeve 240 causes the drive clutch 250 to rotate which, in turn, rotates the leadscrew 253 to which the drive clutch 250 is splined.

Rotation of the leadscrew 253 causes it to advance axially forwards towards the front end 200a of the injection device 200 because of the engagement of the leadscrew thread with the thread of the leadscrew nut 252. The leadscrew nut 252 is rotationally and axially fixed with respect to the housing 212.

During dose setting, the last dose nut 241 is rotationally fixed with respect to the housing 212 via the leadscrew 253. The last dose nut 241 can translate axially up and down the thread inside the drive sleeve 240 due to rotation of the drive sleeve 240 when the dose is being set. Translation of the last dose nut 241 inside the drive sleeve 240 is limited by a rotational stop feature on the drive sleeve 240 which limits the travel of the last dose nut 241 to a position corresponding with the maximum dispense volume of the injection device 200.

During dose delivery, the drive sleeve 240, leadscrew 253 and last dose nut 241 all rotate together and there is no axial translation of the last dose nut 241 with respect to the drive sleeve 240.

Dose Setting—Incrementing the Dose

With the injection device 200 in the configuration shown in FIG. 25, the user grips the dose selector 216 and rotates it clockwise about axis L, with respect to the housing 212, in order to increment the dose and charge the drive spring 220. As the dose selector 216 is turned clockwise, the dose selector 216 is engaged with the ratchet pawl 217, causing it to rotate with the dose selector 216. The ratchet pawl 217 drives the units wheel 218 clockwise because of ratchet fingers 217a engaging ribs 218a of the units wheel 218, as shown in FIG. 25A. The drive spring 220 is hooked into the back of the units wheel 218 and is therefore tightened as the units wheel 218 is rotated. In other words, torque is transferred from the dose selector 216 to the drive spring 220 directly through the dose indicator, i.e. the units wheel 218.

While the dose is being incremented, the ratchet arms 217b on the ratchet pawl 217 engage with teeth 213 on the inside surface of the housing 212 to prevent un-winding of the drive spring 220, as shown in FIG. 25B.

When the dose selector 216 reaches a maximum, minimum or last dose limit, the ratchet fingers 217a flex radially outwardly and skip past the ribs 218a of the units wheel 218 (FIG. 25C).

Dose Setting—Decrementing the Dose

Figure 26:
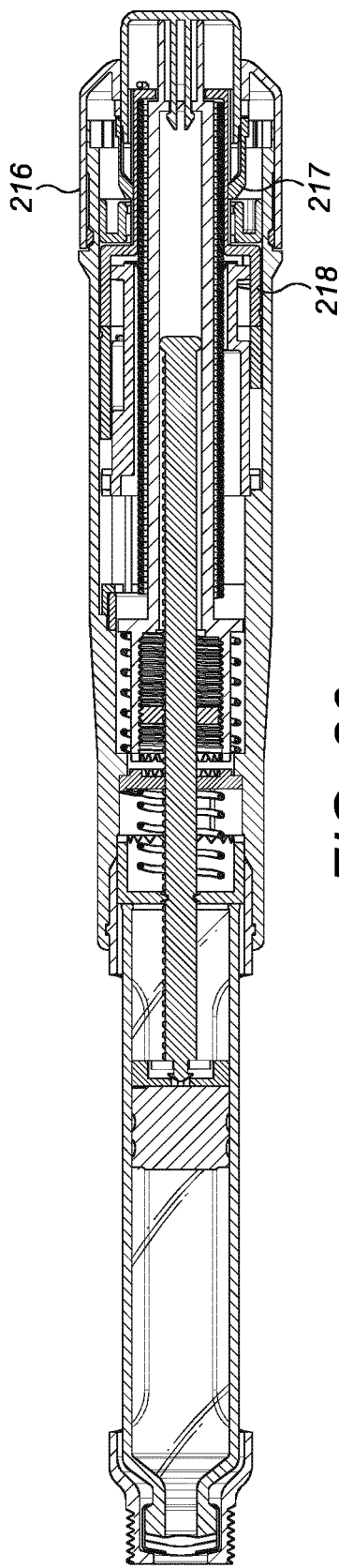
FIGS. 26, 26A and 26B illustrate decrementing the dose.
Figure 26B:
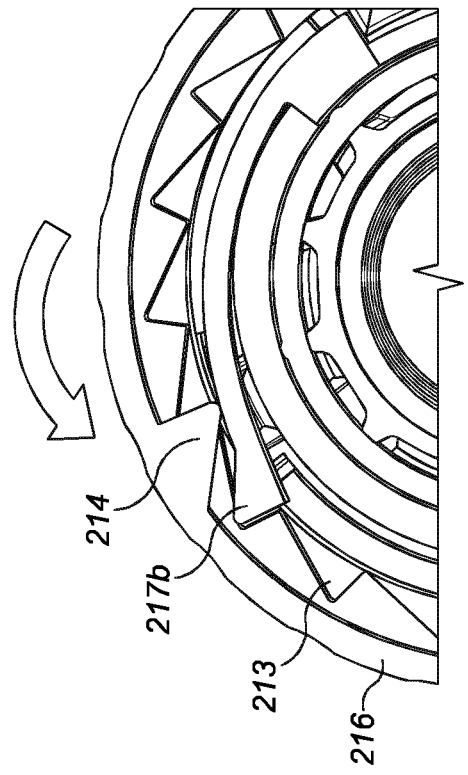
Figure 26A:
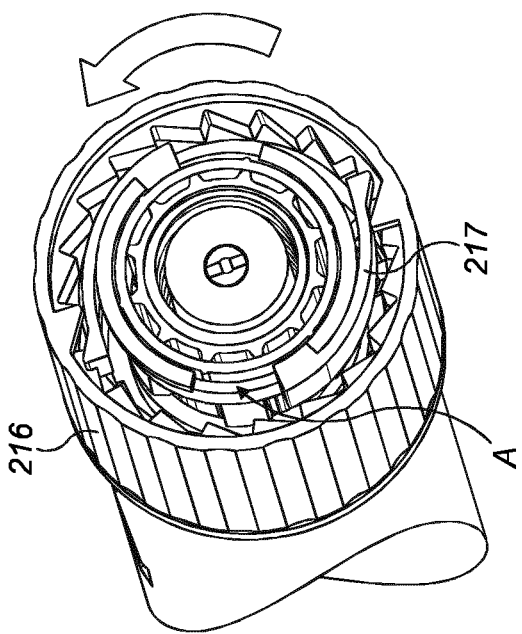

When it is desired to decrement the selected dose, the dose selector 216 is turned anti-clockwise. As shown in FIG. 26A, as the dose selector 216 is turned anti-clockwise, there is a small amount of backlash at point A such that the dose selector 216 can rotate slightly with respect to the ratchet pawl 217. This small relative movement is sufficient to allow tabs 214 on the dose selector 216 to depress the ratchet arms 217b so that they can click past the housing teeth 213, allowing the drive spring to unwind slightly before the ratchet arms 217b catch again on the next housing tooth 213. The tabs 214 may be tooth-shaped formations projecting radially-inwardly from an internal surface of the dose selector 216. This is represented in FIG. 26B. Each decrement preferably equates to 1 IU ("international unit") of medicament.

Dose Delivery

Figure 27:
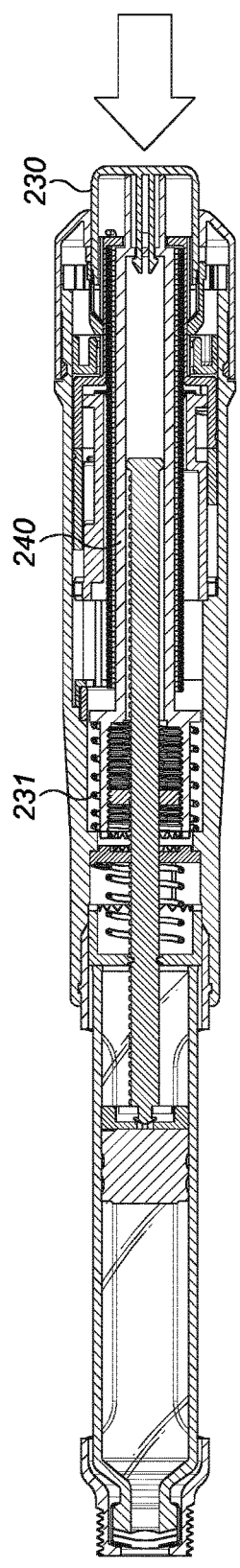
FIGS. 27 and 27A-27F illustrate dose delivery.
Figure 27C:
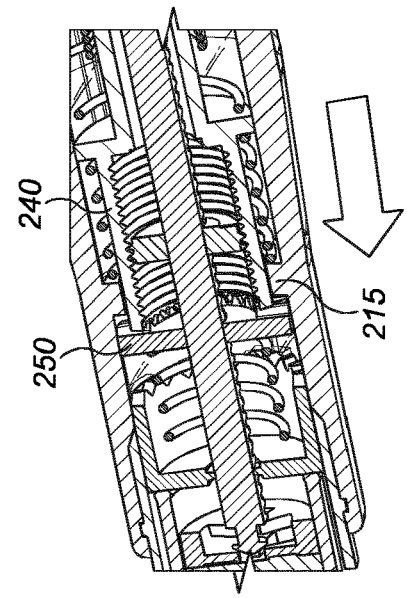
Figure 27B:
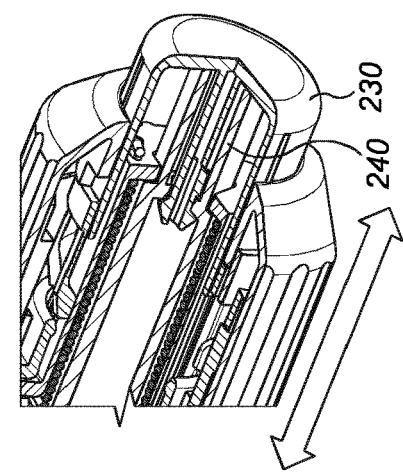
Figure 27A:
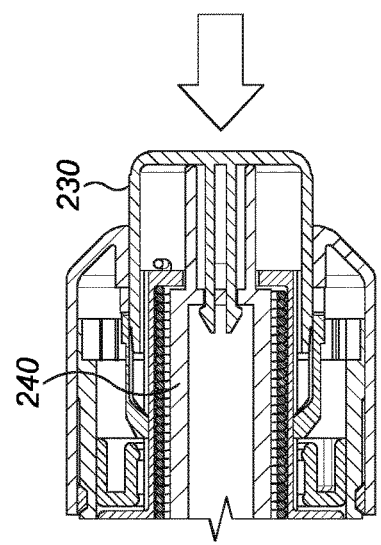

To initiate dose delivery, the user presses the dose button 230 against the bias of the dose button spring 231 as shown in FIG. 27. This pushes the drive sleeve 240 axially forwards. Although the drive sleeve 240 is rotationally locked to the units wheel 218, it is free to slide axially with respect thereto (FIG. 27B).

Figure 27D:
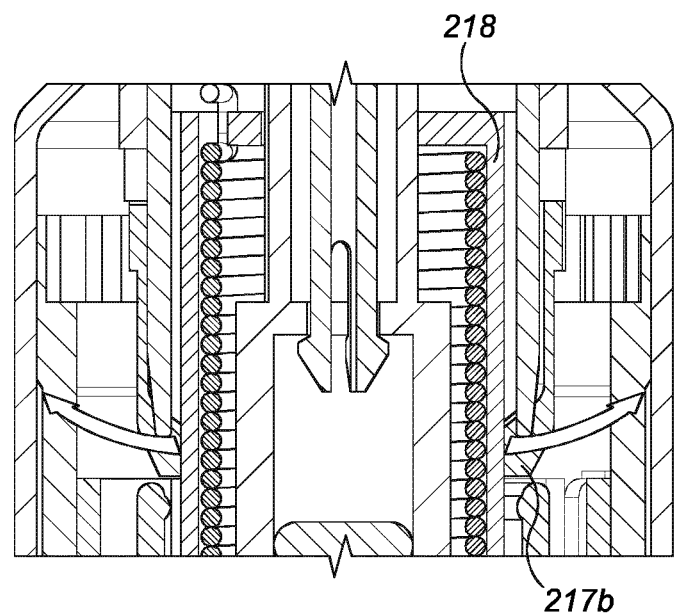
Figure 27E:
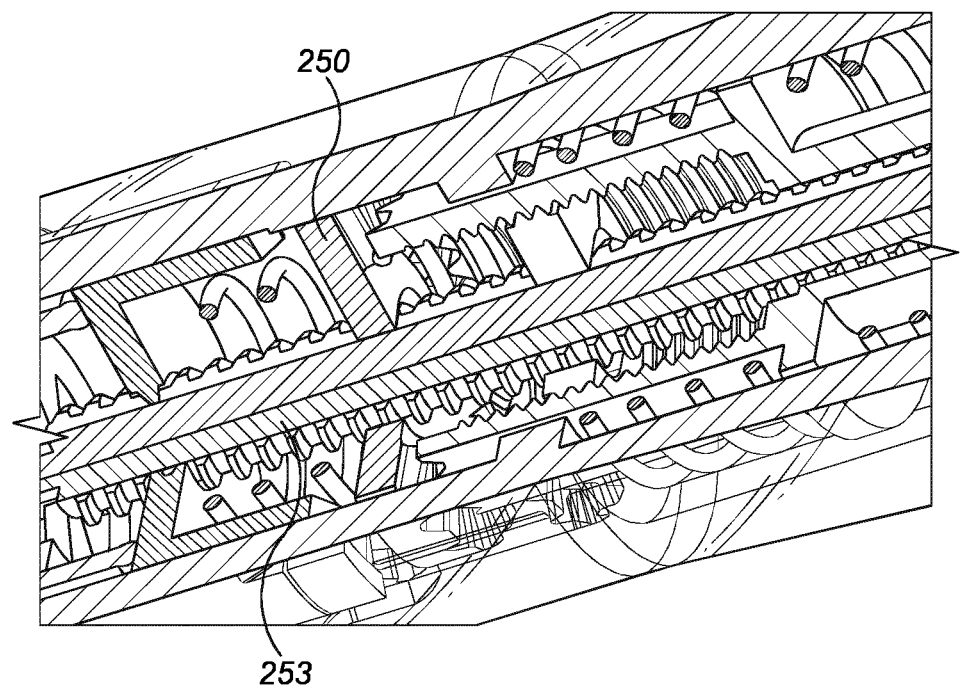

As the drive sleeve 240 advances, its forward end engages the rear surface of the drive clutch 250. The drive clutch 250 disengages from the clutch engaging features 215 on the inside surface of the housing 212 (FIG. 27C). Once the drive clutch 250 is fully engaged with the drive sleeve 240, the dose button 230 disengages the ratchet pawl 217 from the units wheel 218 (FIG. 27D). The units wheel 218 is now free to rotate the drive sleeve 240 and therefore also the drive clutch 250 about longitudinal axis L. The drive clutch 250 is splined to the leadscrew 253 (FIG. 27E).

Figure 27F:
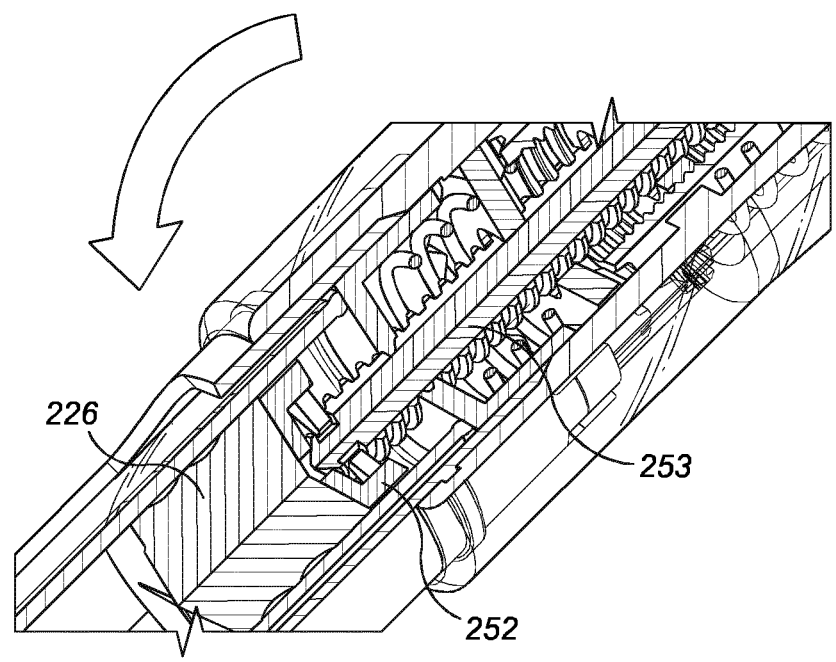

Therefore the leadscrew 253 now rotates and is caused to advance axially due to threaded engagement with the leadscrew nut 252. The thrust bearing 254 advances the cartridge stopper 226 into the cartridge, in order to expel medicament to deliver the selected dose (FIG. 27F).

When the dose button 230 is released, the dose button spring 231 returns the dose button 230 and drive sleeve 240 to their original starting positions. This axially rearward movement disengages the drive clutch 250 and re-engages the ratchet arms 217b with the housing 212 thereby stopping dose delivery.

Dose Delivery—Haptic Feedback

Figure 28:
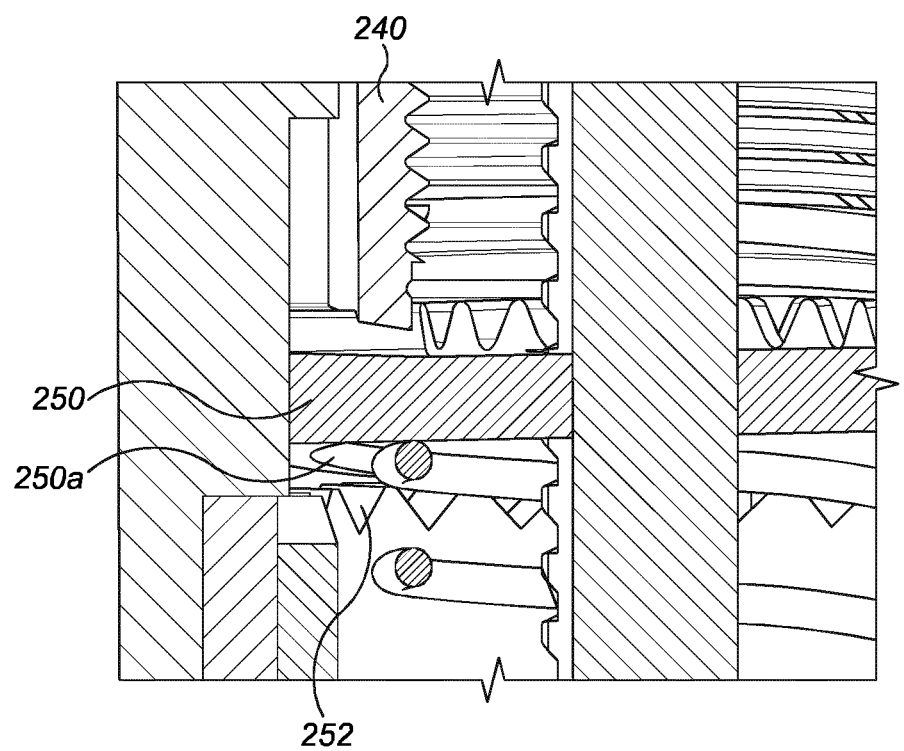
FIG. 28 illustrates a haptic feedback feature.

Referring to FIG. 28, during dose delivery haptic feedback occurs between the drive clutch 250 and the leadscrew nut 252 when the drive clutch 250 is spinning, by virtue of the haptic feedback arm 250a on the drive clutch clicking over axially-rearwardly-facing teeth on the leadscrew nut 252.

Last Dose Protection

When the medicament cartridge 224 is relatively empty, after several doses have already been delivered therefrom, it is undesirable for the user to be able to select a dose that is larger than the available quantity of medicament remaining. Last dose protection is provided to deal with this situation. Last dose protection is provided by the last dose nut 241.

Figure 29:
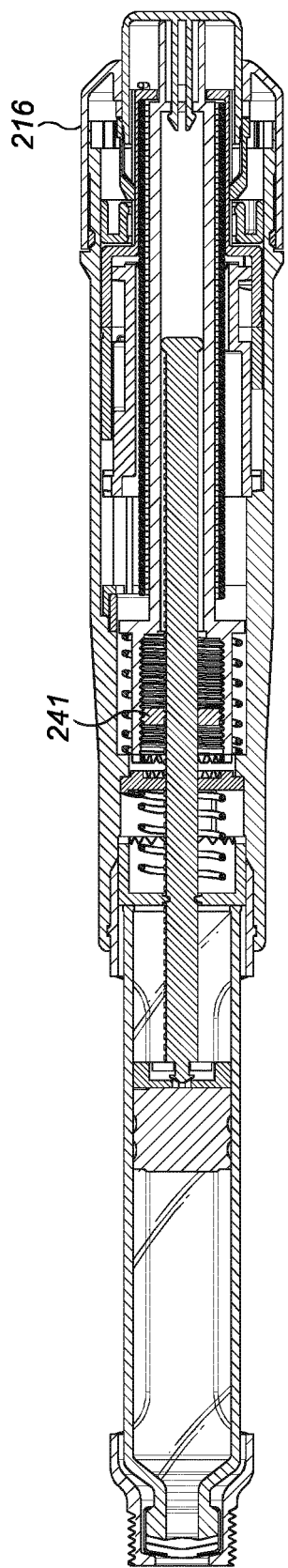
FIGS. 29, 29A and 29B illustrate last dose protection.
Figure 29B:
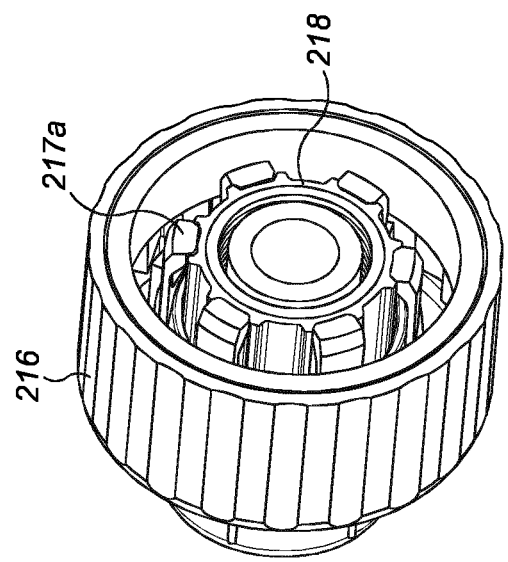
Figure 29A:
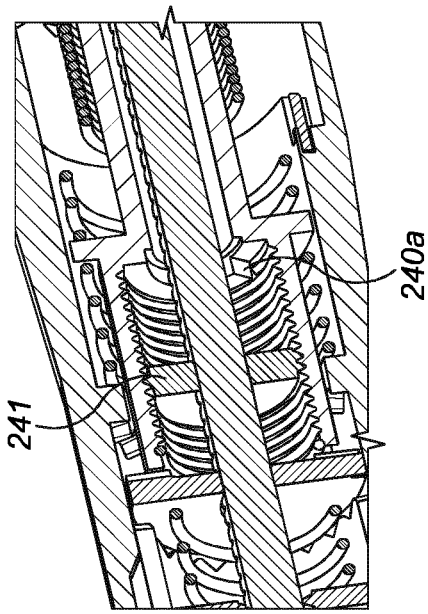
Figures 30, 31, 32:
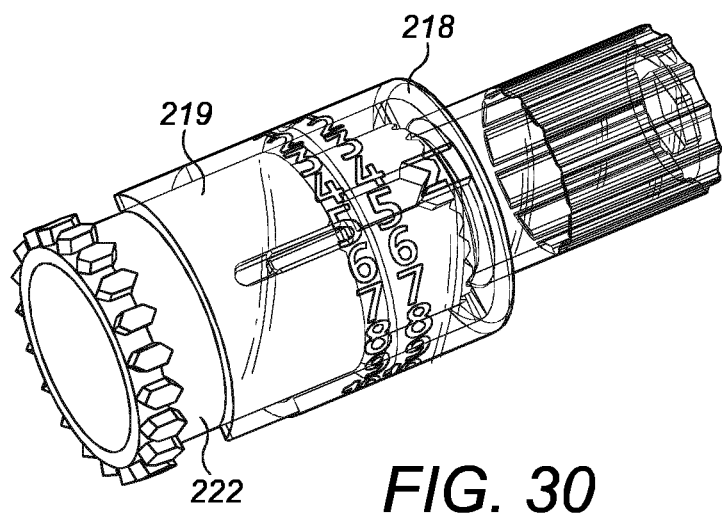
FIG. 30 is a perspective view of the odometer mechanism.
FIG. 31 is a perspective view of the units wheel from the odometer mechanism.
FIG. 32 is a perspective view of the tens wheel from the odometer mechanism.

As shown in FIG. 29A, the last dose nut 241 moves axially forwards and backwards on the thread inside the drive sleeve 240 during dose incrementing and decrementing. When there is less than a predetermined amount (e.g. 100 IU) of medicament remaining in the cartridge 224, the last dose nut 241 stops against a rotary endstop 240a at the rear of the drive sleeve thread.

Engagement of the last dose nut 241 with the endstop 240a means that, should the user attempt to wind the dose selector 216 beyond the remaining dose, the over-torque protection is actuated, preventing the user from damaging the device (FIG. 29B). The ratchet fingers 217a disengage from the units wheel 218 as previously described in relation to FIG. 25C.

Dose Display

Figure 35A:
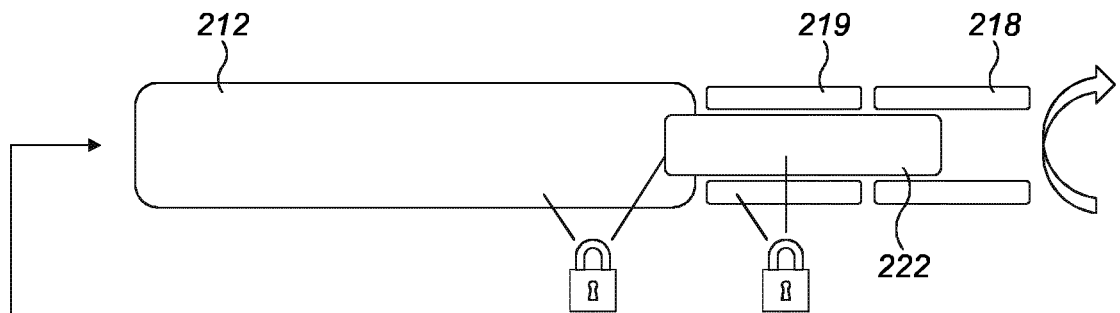
FIGS. 35A-35C show three stages of the odometer mechanism's operation.
Figure 35B:
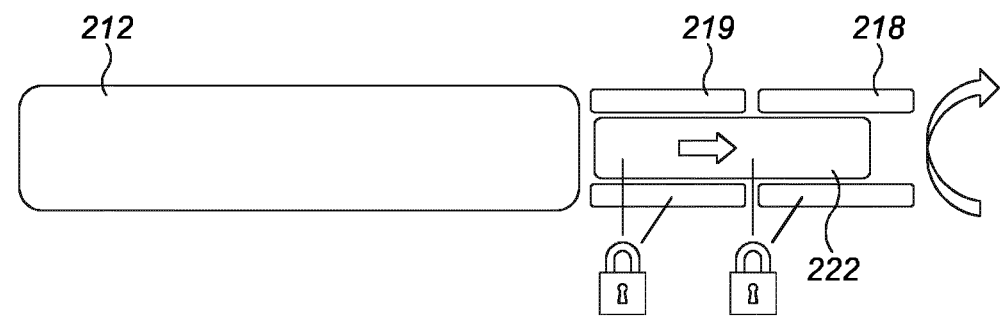
Figure 35C:
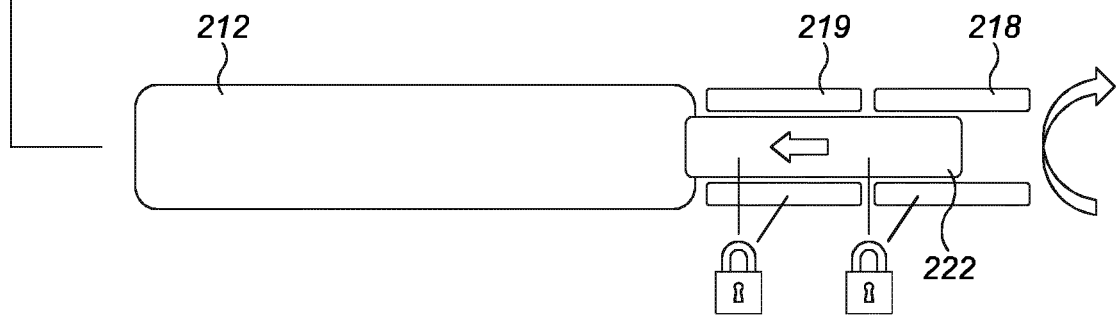
Figure 36:
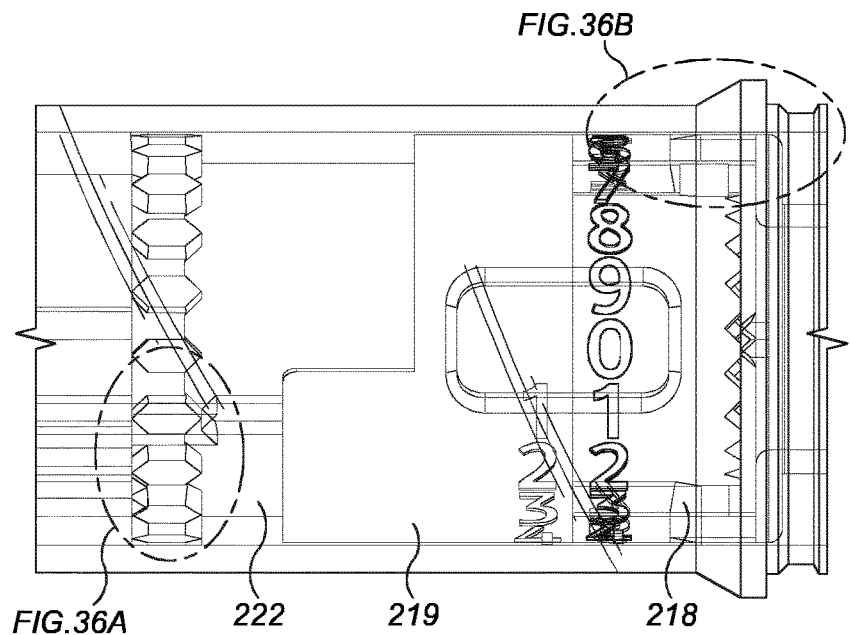
FIGS. 36, 36A and 36B show further detail of the stage illustrated in FIG. 35A.
Figure 37:
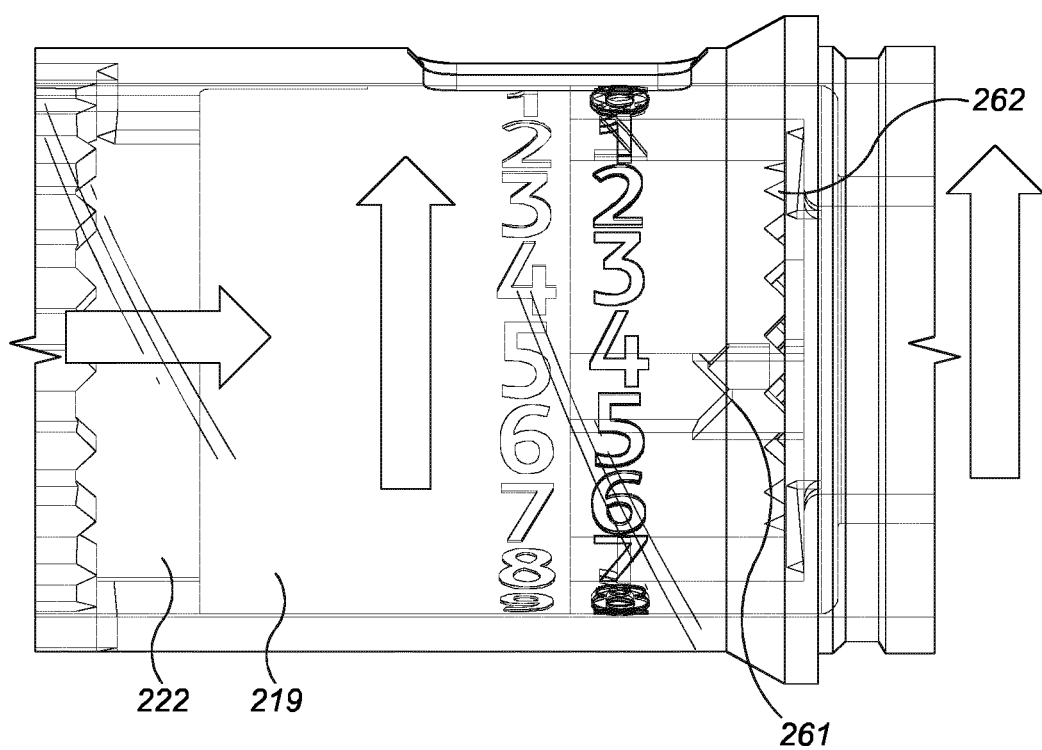
FIG. 37 shows further detail of the stage illustrated in FIG. 35B.
Figure 38:
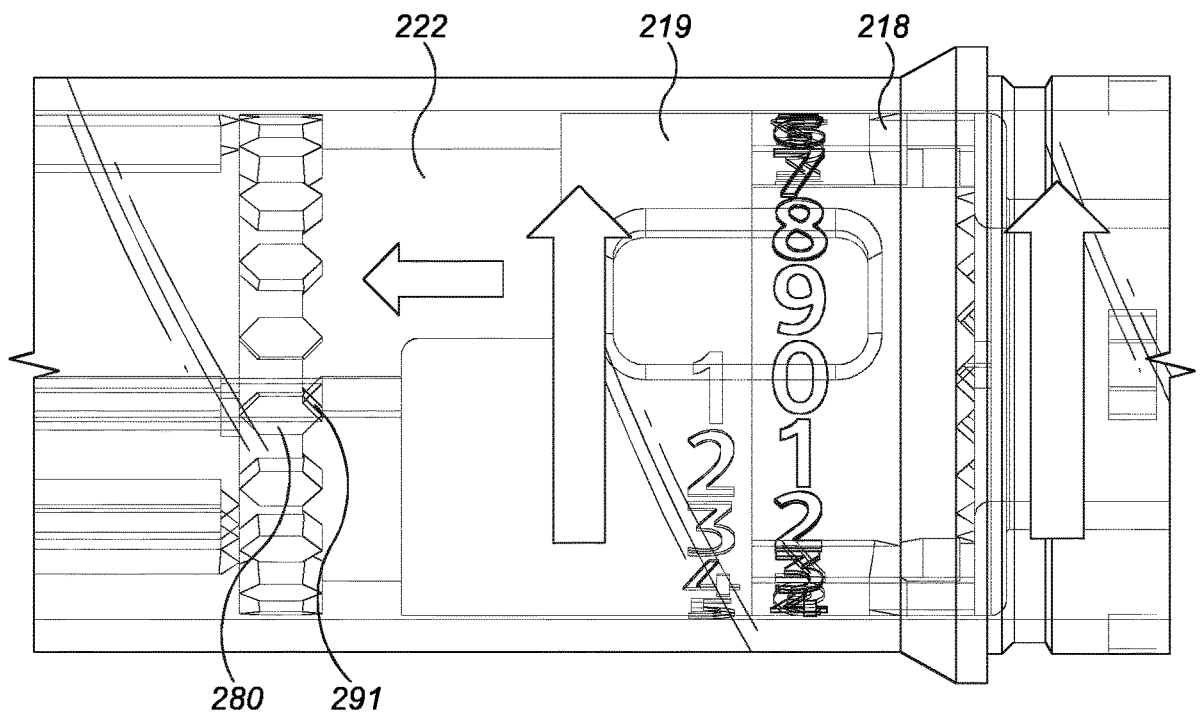
FIG. 38 shows further detail of the stage illustrated in FIG. 35C.

FIGS. 35A-35C show, in schematic form, the three stages of the odometer mechanism's operation. More detail of the respective stages is shown in FIGS. 36-38.

Figure 33:
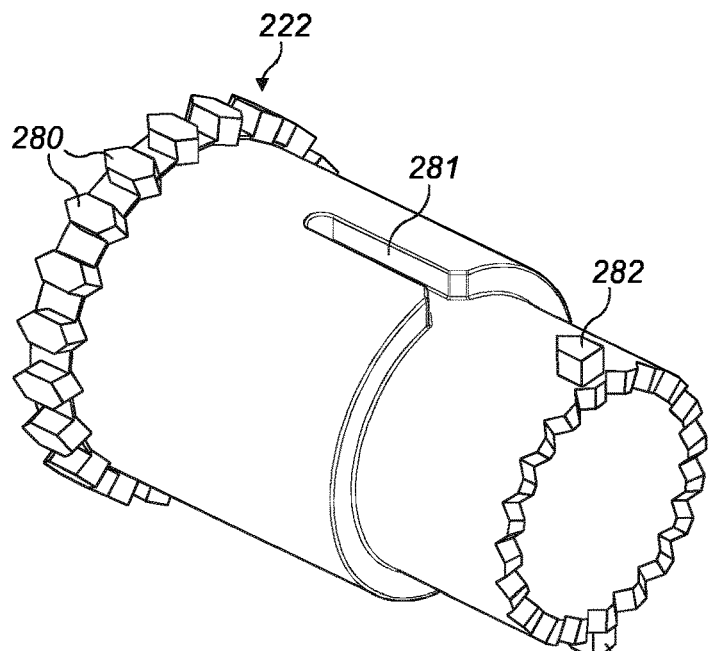
FIG. 33 is a perspective view of the shuttle lock from the odometer mechanism.
Figure 36A:
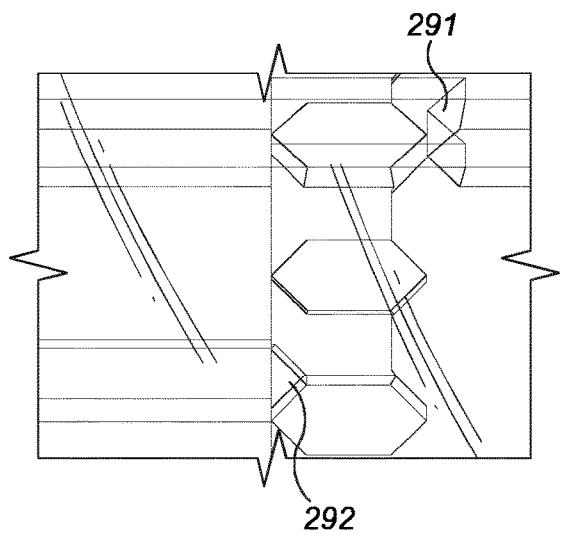
Figure 36B:
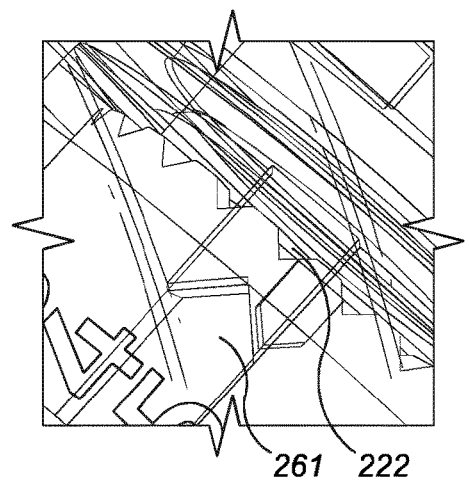

In stage 1 (FIGS. 35A, 36, 36A and 36B) for dose 0-9, the units wheel 218 is free to turn. Rotation of the dose selector 216 causes the dose to increment through doses 0-9. For doses 0-9, there is no engagement between the units wheel drive dogs 261 and the shuttle lock dogs 282 (FIG. 36B). The tens wheel 219 is rotationally locked but is axially moveable relative to the shuttle lock 222 because the key 273 is engaged in the keyway 281 (see FIG. 30). The shuttle lock 222 is rotationally locked to the housing 212 because the housing engagement ribs 292 (FIG. 36A) are engaged with three of the shuttle lock peripheral teeth 280 (FIG. 33).

After the units wheel has reached dose "9", in stage 2 (FIG. 35B and FIG. 37), the drive dogs 261 of the units wheel 218 engage shuttle lock dogs 282 during dose "10". The engagement of the angled faces of the dogs 261, 282, causes a camming action that moves the shuttle lock 222 axially rearwardly enough to disengage the shuttle lock peripheral teeth 280 from the housing engagement ribs 292. The shuttle lock 222 is therefore no longer rotationally locked to the housing 212. Since the key 273 is axially moveable in the keyway 281, the shuttle lock 222 is able to move axially relative to the tens wheel 219. Consequently, the tens wheel 219 itself does not move axially and the tens numbers 270 remain in a position adjacent to the units numbers 260. The axially rearward movement of the shuttle lock 222 causes angled faces of the dogs 261, 282 to reach the end of their sloping engagement, at which point the shuttle lock rear teeth 283 engage the axially-extending splines 262 on the units wheel 218. This rotationally locks the units wheel 218 and the shuttle lock 222 together.

The units wheel 218 is still able to turn. The tens wheel 219 is still rotationally locked to the shuttle lock 222 by virtue of the key 273 engaging in the keyway 281. Because the shuttle lock 222 (and hence the tens wheel 219 rotationally locked thereto) is rotationally locked to the units wheel 218 by the engagement of the units wheel splines 262 with the shuttle rear teeth 283, further turning of the units wheel 218 causes the shuttle lock 222 and the tens wheel 219 to rotate together.

After 9° of rotation of the shuttle lock 222 and tens wheel 219 by the units wheel 218, stage 3 is reached (FIG. 35C and FIG. 38), in which two of the shuttle lock peripheral teeth 280 come into contact with the angled faces of the two housing dogs 291.

Then, for the next 9° of rotation, the camming action of the angled faces of the housing dogs 291 and those of the shuttle lock peripheral teeth 280 cause the shuttle lock 222 to revert axially to re-engage the housing engagement ribs 292 so that the shuttle lock 222 is once again rotationally locked to the housing 212. Axial reversion of the shuttle lock 222 to its stage 1 forward position also causes the shuttle lock rear teeth 283 to disengage from the splines 262 on the units wheel 218. In this example, for every 18° of rotation (9°+9°), the shuttle lock completes a full cycle as described above. Other angles of rotation for each cycle are possible.

This completes the number change of the tens wheel 219. The mechanism functions in reverse if the dose is decremented.

Dose Setting—Maximum/Minimum Dose Limit

Figure 39A:
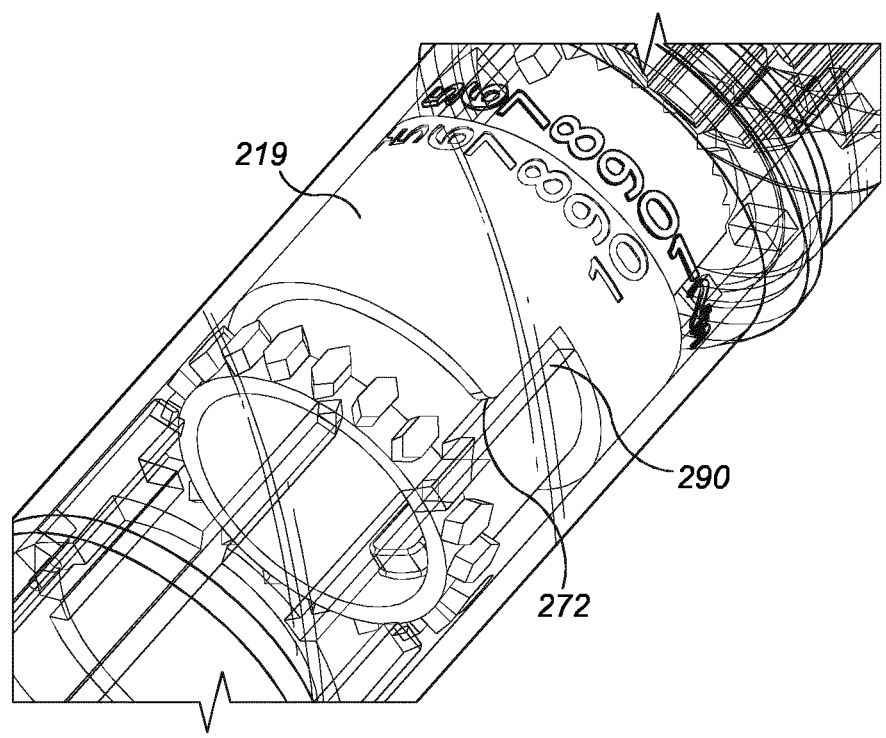
FIGS. 39A and 39B illustrate maximum/minimum dose limiting.
Figure 39B:
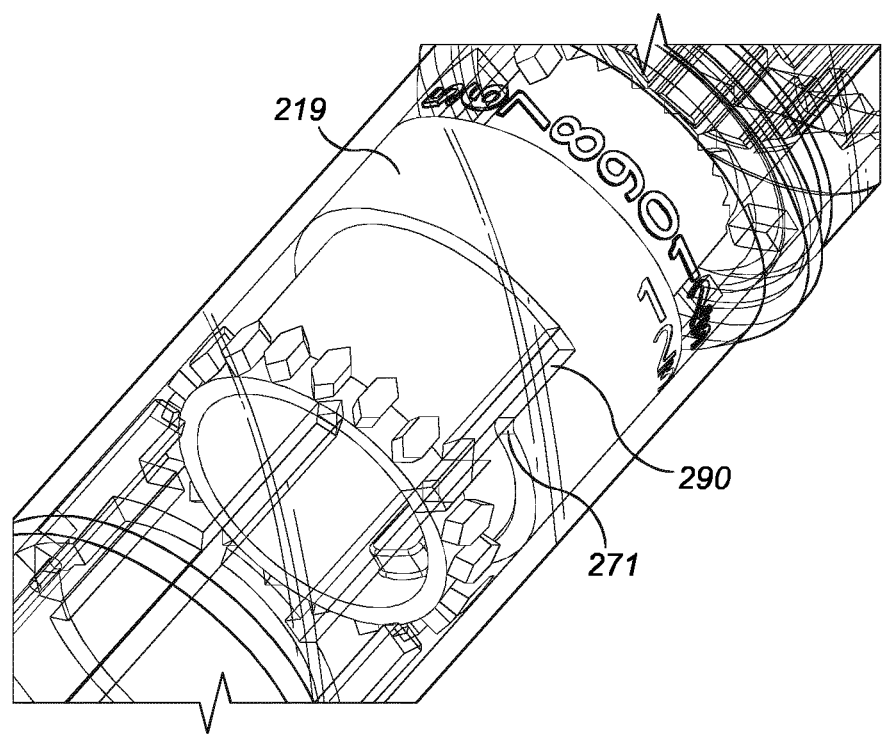

Limiting the maximum/minimum dose that can be set by the dose selector 216 is realised by cut out features 271, 272 on the tens wheel 219 which interact with a limit rib 290 on the housing. One side of the rib 290 limits the tens wheel at the minimum dose when feature 272 is rotated into abutment with the rib 290 (FIG. 39A). The other side of the rib 290 limits the tens wheel at the maximum dose, typically 100 IU, when feature 271 is rotated into abutment with the rib 290 (FIG. 39B). As mentioned above, the rib 290 is an extended part of one of the housing dogs 291 for engaging the shuttle lock 222.

Figure 40:
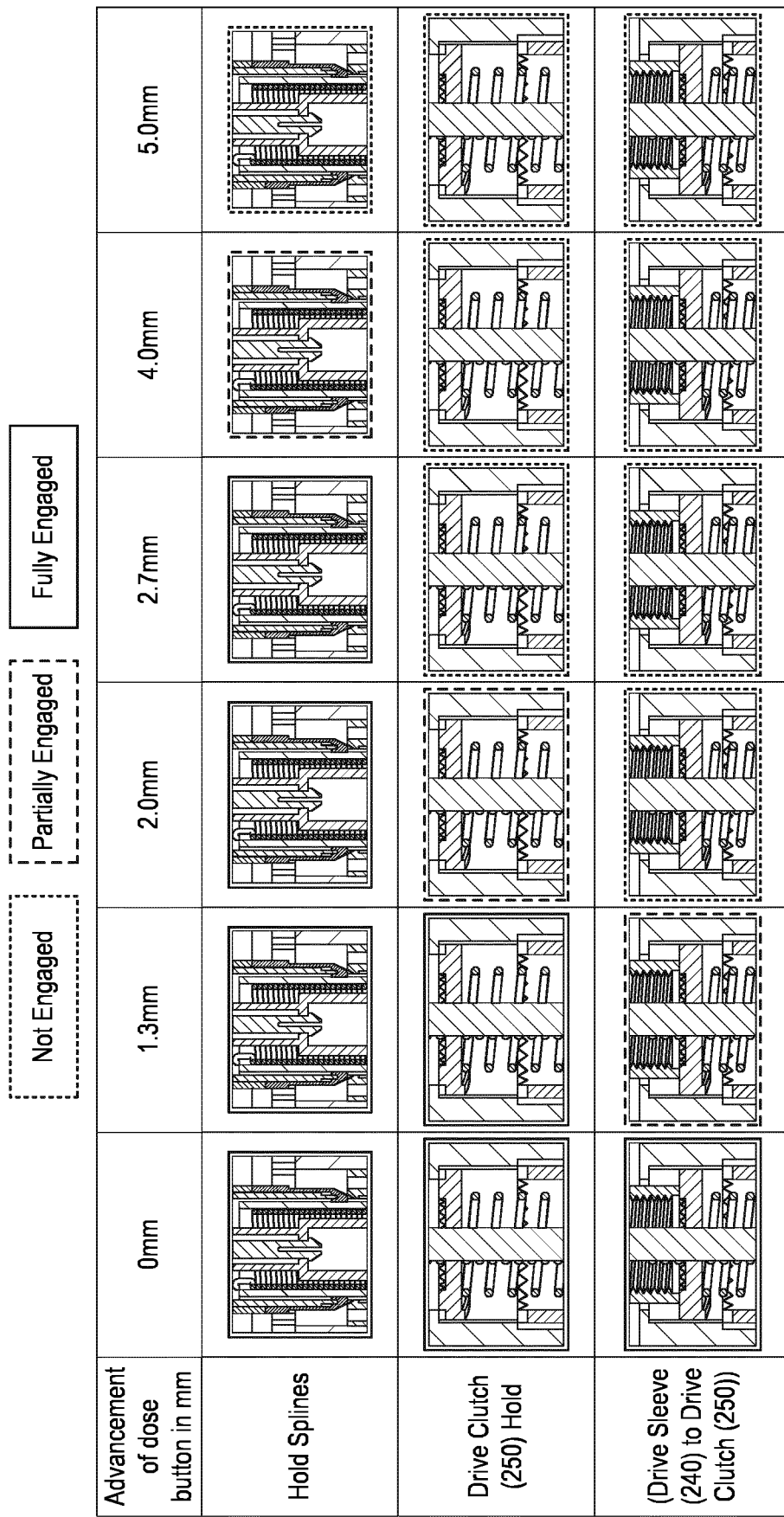
FIG. 40 is a diagrammatic summary of the key engagement points of the components of the injection device of FIG. 20, at six stages of dose delivery.

FIG. 40 is a diagrammatic summary of the key engagement points of the injection device components, at six stages of dose delivery. Example distances of advancement of the dose button 230, starting at 0 mm, are shown. For each distance, each of the hold splines (ratchet pawls 217), drive clutch 250 and drive sleeve 240/drive clutch 250 are indicated as being either not engaged (dotted box outline), partially engaged (dashed box outline) or fully engaged (solid box outline).

As with the first embodiment, described with reference to FIGS. 1-3, the drive spring 220 is coupled to the units wheel 218 such that a charging force can be transferred from the dose selector 216 to the spring 220 via the units wheel 218 to increase the energy stored by the spring 220. By coupling the spring 220 to the units wheel 218, a more accurate dose indication may be achieved. When the dose selector 216 is rotated by a user, the dose indicator (units wheel 218 and tens wheel 219), which is in series therewith serves a dual function of both displaying the currently selected dose and also transferring the charging force from the dose selector in order to charge the drive spring 220.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

REFERENCE NUMERALS 10 injection device
L longitudinal axis
10a front end of the device
10b rear end of the device
12 housing
12a aperture in the housing
14 needle
16 dose selector
16a first plurality of teeth on dose selector
18 dose indicator
18a second plurality of teeth on dose indicator
20 spring
20a first end of the spring
20b second end of the spring
22 drive assembly
24 medicament container
26 force path
100 injection device
L longitudinal axis (housing)
Lc second longitudinal axis (cartridge)
100a front end of the device
100b rear end of the device
107 units housing feature
108 tens housing feature
109 housing ridge features
110 housing smooth inside surface track
111 housing ramps for drive shaft ratchet arms
112 housing
112a aperture in the housing
113 housing teeth
114 tabs
115 dose selector pawl
116 dose selector
117 dose indicator spring
118 units wheel
118a teeth on units wheel (for engaging tens wheel)
118b formation on units wheel (for engaging units housing feature)
119 tens wheel
119a teeth on tens wheel (for engaging units wheel)

119b formations on tens wheel (for engaging tens housing feature)
120 drive spring
124 medicament cartridge
125 cartridge holder
126 cartridge stopper
130 dose button
131 dose button spring
140 drive shaft
141 dose limit nut
141a dose limit nut endstop feature for max dose limiting and last dose limiting
141b dose limit nut endstop feature for min dose limiting
142 worm gear
143 worm gear support
144 worm gear rotational lock
145 plunger rack
146 drive shaft ratchet arms
147 max dose endstop on plunger rack for dose limit nut
148 min dose endstop on plunger rack for dose limit nut
149 drive shaft splines
150 worm gear clutch
A backlash point for over-torque protection
200 injection device
200a front end of the device
200b rear end of the device
L longitudinal axis
212 housing
212a aperture in housing
213 housing teeth
214 tabs on housing
215 clutch engaging feature on housing
216 dose selector
217 ratchet pawl
217a ratchet fingers
217b ratchet arms
218 units wheel
218a units wheel ribs
219 tens wheel
220 drive spring
221 housing top cap
222 odometer shuttle lock
224 medicament cartridge
225 cartridge holder
226 cartridge stopper
230 dose button
231 dose button spring
240 drive sleeve
240a last dose nut endstop
241 last dose nut
250 drive clutch
250a haptic feedback arm
251 drive clutch spring
252 leadscrew nut
253 leadscrew
254 thrust bearing
260 units numbers
261 units wheel drive dogs
262 units wheel engagement splines
270 tens numbers
271 max dose limit feature
272 min dose limit feature
273 tens wheel key to engage shuttle lock
280 shuttle lock peripheral teeth
281 shuttle lock keyway
282 shuttle lock dogs
283 shuttle lock rear teeth
290 housing max/min limit rib
291 housing dogs for engaging shuttle lock
292 housing engagement ribs
A backlash point for dose decrementing

The invention claimed is:

1. An injection device comprising:
   a. a housing having a longitudinal axis;
   b. an axially-depressible dose button,
   c. a dose indicator comprising an odometer positioned within the housing and arranged about said longitudinal axis;
   d. a dose selector operatively connectable in series to the dose indicator, the dose selector and the dose indicator being capable of cooperating with one another to set a dose to be ejected from the injection device; and
   e. a spring capable of storing energy necessary for ejecting the dose from the injection device;
   wherein the spring is locked at one end to the dose indicator such that a charging force can be transferred in series from the dose selector to the spring via the dose indicator, when the dose selector is operatively connected to the dose indicator, to increase the energy stored by the spring;
   wherein the odometer comprises a units wheel operatively connected to the dose selector so that rotation of the dose selector also rotates the units wheel, and a tens wheel selectively engageable with the units wheel so that rotation of the units wheel also rotates the tens wheel, and wherein the spring is coupled to the units wheel.

2. The injection device of claim 1 wherein the dose selector is operatively connectable to the dose indicator via a ratchet pawl, the ratchet pawl releasably engaging the dose selector and preventing counter-rotation of the dose indicator during dose setting, the ratchet pawl being disengageable from the dose selector by axial depression of the dose button.

3. The injection device of claim 2 wherein said charging force can be transferred from the dose selector to the spring via the engaged ratchet pawl and dose indicator.

4. The injection device of claim 1 wherein the spring is a torsion spring and the charging force transferred to the spring is a charging torque.

5. The injection device of claim 4 further comprising a drive assembly having a rotational to axial coupling, where the drive assembly is rotationally drivable by the torsion spring and is arranged to provide an axial force for ejecting the dose from the injection device.

6. The injection device of claim 5 wherein the drive assembly is rotationally drivable by the torsion spring via the dose indicator.

7. The injection device of claim 1 wherein the spring is directly locked to the dose indicator.

8. The injection device of claim 1 wherein the spring is locked to the dose indicator via one or more intermediate components capable of transmitting the charging force.

9. The injection device of claim 1 wherein the dose selector is directly coupled to the dose indicator.

10. The injection device of claim 1 wherein the dose selector is coupled to the dose indicator via one or more intermediate components capable of transmitting the charging force.

11. The injection device of claim 1 wherein the dose indicator is marked with a sequence of numbers or symbols, at least one of the numbers or symbols being visible through an aperture or window in the housing.

12. The injection device of claim 1 further comprising a medicament container.

13. The injection device of claim 12 wherein the medicament container comprises a pre-filled syringe or cartridge.

14. The injection device of claim 12 further comprising a medicament contained in the medicament container.

15. The injection device of claim 14 wherein the medicament is selected from the group comprising: antipsychotic substances including risperidone, hormones, antitoxins, substances for the control of pain, immunosuppressives, substances for the control of thrombosis, substances for the control or elimination of infection, peptides, proteins, human insulin or a human insulin analogue or derivative, polysaccharide, DNA RNA, enzymes, antibodies, oligonucleotide, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity.

* * * * *